United States Patent
Narayanan et al.

(10) Patent No.: US 11,651,838 B2
(45) Date of Patent: May 16, 2023

(54) AUTOMATED PREDICTION OF BIOLOGICAL RESPONSE OF CHEMICAL COMPOUNDS BASED ON CHEMICAL INFORMATION

(71) Applicant: Tata Consultancy Services Limited, Mumbai (IN)

(72) Inventors: Ramamurthi Narayanan, Hyderabad (IN); Geervani Koneti, Hyderabad (IN); Dipayan Ghosh, Hyderabad (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 780 days.

(21) Appl. No.: 16/535,025

(22) Filed: Aug. 7, 2019

(65) Prior Publication Data
US 2020/0303041 A1    Sep. 24, 2020

(30) Foreign Application Priority Data
Mar. 22, 2019   (IN) .............................. 201921011056

(51) Int. Cl.
*G16C 20/30*    (2019.01)
*G16C 20/20*    (2019.01)
(Continued)

(52) U.S. Cl.
CPC ............ *G16C 20/30* (2019.02); *G16C 20/20* (2019.02); *G16C 20/50* (2019.02); *G16C 20/64* (2019.02); *G16C 20/70* (2019.02); *G16C 20/90* (2019.02)

(58) Field of Classification Search
CPC ......... G16C 20/30; G16C 20/40; G16C 20/70
See application file for complete search history.

(56) References Cited

U.S. PATENT DOCUMENTS 9,162,753 B1   10/2015  Panto et al.
9,911,340 B2    3/2018  Samarasekera et al.
(Continued)

OTHER PUBLICATIONS

Hu, L. et al. (Dec. 2011). "Predicting Biological Functions of Compounds Based on Chemical-Chemical Interactions," *PLoS One*, vol. 6, No. 12; pp. 1-9.
(Continued)

*Primary Examiner* — Lam S Nguyen
(74) *Attorney, Agent, or Firm* — Finnegan, Henderson, Farabow, Garrett & Dunner LLP

(57) ABSTRACT

Lack of safety and efficacy are the two major unwanted biological responses that play as critical bottlenecks for the success of drug candidates in drug discovery and development. Conventional systems and methods involve ineffective exploration and use of chemical information space and thereby, may fail to address safety and efficacy issues. Embodiments of the present disclosure provides an effective solution to the above bottle-necks with the effective exploration/search of chemical information space using effective statistical techniques that yield meaningful chemical information comprising relevant descriptors, fingerprints, fragments, optimized set of structural images, and the like. Further, it provides robust predictive models for the biological response, example renal toxicity using the selected chemical information in an automated manner for a given experimental data and alerts/rules that can be successfully employed to address failures of drug candidates during discovery and development.

20 Claims, 11 Drawing Sheets

(51) Int. Cl.
  *G16C 20/64* (2019.01)
  *G16C 20/90* (2019.01)
  *G16C 20/50* (2019.01)
  *G16C 20/70* (2019.01)

(56) References Cited

U.S. PATENT DOCUMENTS

| | | | | |
|---|---|---|---|---|
| 2002/0077754 | A1* | 6/2002 | McGregor | G16C 20/60 435/7.1 |
| 2004/0199334 | A1* | 10/2004 | Kovesdi | G16C 20/30 703/11 |
| 2012/0290624 | A1* | 11/2012 | Singh | G06F 16/00 707/E17.044 |
| 2018/0321692 | A1 | 11/2018 | Castillo-Effen et al. | |
| 2019/0019589 | A1 | 1/2019 | Waite | |

OTHER PUBLICATIONS

Safizadeh, H. et al. (Mar. 2017) "Improving prediction of compound function from chemical structure using chemical-genetic networks," located at < http://dx.doi.org/10.1101/112698>; 28 pages.

* cited by examiner

AUTOMATED PREDICTION OF BIOLOGICAL RESPONSE OF CHEMICAL COMPOUNDS BASED ON CHEMICAL INFORMATION

PRIORITY CLAIM

This U.S. patent application claims priority under 35 U.S.C. § 119 to: India Application No. 201921011056, filed on Mar. 22, 2019. The entire contents of the aforementioned application are incorporated herein by reference.

TECHNICAL FIELD

The disclosure herein generally relates to prediction of biological responses, and, more particularly, to automated prediction of biological response of chemical compounds using chemical information and data analytics workflow associated thereof.

BACKGROUND

Lack of safety and efficacy are the two major reasons for the failures of drug candidates in drug discovery and development. These failures can be addressed using reliable and easily applicable predictive ADMET (biological response) models [Absorption, Distribution, Metabolism, Excretion & Toxicity] at early discovery stage as they rationalize experimental observations. Structure-activity relationships models are one such class of predictive models that are typically generated from a) in vitro (or) in vivo experimental data b) a large number of structural features that are derived from drug candidate's chemical structure and c) statistical techniques that are employed to perform i) training and test set data selection and ii) regression and classification techniques. Therefore, modelling of biological data obtained from various experiments, followed by prediction of responses of new compounds, is an important problem and reliable solution/s to this problem will enable better understanding of the underlying biological processes that determine the biological responses of chemical compounds, for example toxicity, inhibitory concentration (potency), etc. and offer potential to reduce the cost of drug discovery and development.

Besides conventional biochemical experiments, recently, computational methods have been chosen as a promising approach for the understanding of biological functions/responses of chemical compounds and also for the prediction of biological responses of new chemicals based on the insights/learnings with the use of machine learning techniques on the experimental data. The term, "Biological response" can be toxicity of chemicals, potency of drug candidates against a biological target in an in in vitro assay or in a cell based assay etc. It can be defined as the response exhibited by a biological system in in vitro, ex-vivo, in vivo conditions on exposure to a chemical, drug candidate etc. While various machine learning techniques have been used to predict the biological responses of chemical compounds based on chemical structures, the applications of many of these techniques for the prediction of responses of new compounds are less than satisfactory. The less than satisfactory applicability may be attributed to 1) ineffective pre-processing of biological data 2) limited exploitation of chemical information/features that contribute to the biological response 3) inappropriate/ineffective use of approaches (an approach comprises the use of one or more mathematical methods in an effective sequence) or mathematical methods/algorithms for modelling studies and others. Therefore, there are many opportunities to address these limitations with solutions that address better 1) imbalance nature of data set 2) data pre-processing 3) effective exploration of chemical information with appropriate algorithms, rules etc. Reliable solutions to the challenges listed above will result in a) better understanding of the biological responses to chemical compounds in animals and humans, b) discover effective new therapy and c) offer potential to minimize the problems faced by humanity because of drug and chemical related toxicities.

SUMMARY

Embodiments of the present disclosure present technological improvements as solutions to one or more of the above-mentioned technical problems recognized by the inventors in conventional systems. For example, in one aspect, there is processor implemented method for automated prediction of biological response of a chemical compound using chemical information associated thereof. The method comprises receiving biological data pertaining to chemical structure of a chemical compound; generating a plurality of chemical information for the chemical compounds from associated molecular structures, wherein the plurality of chemical information comprise a plurality of physico-chemical and structural descriptors, a plurality of Molecular Fingerprints (MFs), a plurality of molecular fragments, and a plurality of two-dimensional (2D) and three-dimensional (3D) structural images; applying one or more statistical analysis techniques on the plurality of chemical information to obtain filtered chemical information. The step of applying one or more statistical analysis techniques on the plurality of chemical information to obtain filtered chemical information comprises: obtaining a filtered set of descriptors using a plurality of physico-chemical and structural descriptors; generating a plurality of fingerprint categories based on a plurality of molecular fingerprints, wherein a first fingerprint category comprises a first set of fingerprints that is selected based on an occurrence threshold, wherein a second fingerprint category comprises a second set of fingerprints that is selected by applying at least one of a Chi-squared test and a Fisher's exact test on a plurality of molecular fingerprints wherein a third fingerprint category comprises a third set of fingerprints that is selected by applying an information gain statistical test on a plurality of molecular fingerprints; generating a fourth fingerprint category comprising a fourth set of fingerprints that is selected based on a combination of a plurality of molecular fingerprints and a plurality of molecular fragments and the occurrence threshold; and performing one or more transformation techniques on a plurality of two-dimensional (2D) and three-dimensional (3D) structural images to obtain an optimized set of structural images.

The method further comprises automatically generating a plurality of models based on the filtered set of descriptors, the first set of fingerprints, the second set of fingerprints, the third set of fingerprints, the fourth set of fingerprints, and the optimized set of structural images respectively; automatically selecting and recommending a best model from the plurality of models based on the biological data and the plurality of chemical information; and automatically predicting biological response of the chemical compounds based on at least one of the best models and one or more user selected models from the plurality of models.

In an embodiment, the first set of fingerprints, the second set of fingerprints, the third set of fingerprints, and the fourth set of fingerprints comprise one or more CDK fingerprints, one or more CDK Extended fingerprints, one or more Estate fingerprints, one or more CDK Graph only fingerprints, one or more MACCS fingerprints, one or more Pubchem fingerprints, one or more Substructure fingerprints, one or more Klekota-Roth fingerprints, 2D Atom Pair fingerprints, one or more molecular fragments or combinations thereof.

In an embodiment, the first set of fingerprints comprises at least one of a Type I fingerprint, a Type II fingerprint, a Type III fingerprint and a Type IV fingerprint.

In an embodiment, the second set of fingerprints comprises a Type A fingerprint and a Type B fingerprint.

In an embodiment, the third set of fingerprints comprises a Type C fingerprint.

In an embodiment, the fourth set of fingerprints comprises at least one of a Type I fingerprint, a Type II fingerprint, a Type III fingerprint and a Type IV fingerprint.

In an embodiment, the step of applying one or more statistical analysis techniques on the plurality of physico-chemical and structural descriptors to obtain a filtered set of statistically significant descriptors comprises eliminating information having zero or low variance and the like from data specific to the plurality of physico-chemical and structural descriptors.

In an embodiment, a presence of Type I fingerprint in at least one of the first set of fingerprints and the fourth set of fingerprints indicates contribution of the Type I fingerprint to one of a biological response, an adverse event or an activity of the chemical compound, examples: potency of a chemical, drug, toxicity of a chemical or drug, etc.

In an embodiment, an absence of a Type II fingerprint in at least one of the first set of fingerprints and the fourth set of fingerprints indicates contribution of the Type II fingerprint to one of a biological response, an adverse event or an activity of the chemical compound, examples: potency of a chemical, drug, toxicity of a chemical or drug, etc.

In an embodiment, a presence of a Type III fingerprint in at least one of the first set of fingerprints and the fourth set of fingerprints indicates contribution of the Type III fingerprint in no activity, no adverse event, or non-toxicity of the chemical compound.

In an embodiment, an absence of a Type IV fingerprint in at least one of the first set of fingerprints and the fourth set of fingerprints indicates contribution of the Type IV fingerprint in no activity, no adverse event, or non-toxicity of the chemical compound.

In an embodiment, a first model (or Model I) from the plurality of models is generated based on the filtered set of descriptors, the first set of fingerprints, classification models such as support vector machine and random forest or combinations thereof.

In another embodiment, a second model (Model II) from the plurality of models is generated based on the first set of fingerprints, and occurrence of each type of first set of fingerprints in a chemical compound.

In an embodiment, the third model (Model III) is generated based on a probability of at least one of at least one of the activity, biological response or adverse event levels (for example toxic and non-toxic) in the second set of fingerprints and the third set of fingerprints.

In an embodiment, the fourth model (Model IV) is generated based on the fourth set of fingerprints and occurrence of each type of fourth set of fingerprints in a chemical compound.

In an embodiment, the fifth model (Model V) is generated based on generated two-dimensional (2D) and three-dimensional (3D) structural images of chemical compounds and classification techniques such as deep neural networks.

In another aspect, there is processor implemented system for automated prediction of biological response of a chemical compound using chemical information associated thereof. The system comprises a memory storing instructions; one or more communication interfaces; and one or more hardware processors coupled to the memory via the one or more communication interfaces, wherein the one or more hardware processors are configured by the instructions to: receive biological data pertaining to chemical structure of a chemical compound; generate a plurality of chemical information for the chemical compound using associated molecular structure, wherein the plurality of chemical information comprise a plurality of physico-chemical and structural descriptors, a plurality of Molecular Fingerprints (MF), a plurality of molecular fragments, and a plurality of two-dimensional (2D) and three-dimensional (3D) structural images; apply one or more statistical analysis techniques on the plurality of chemical information to obtain filtered chemical information, wherein the step of applying one or more statistical analysis techniques on the plurality of chemical information to obtain the filtered chemical information comprises: obtaining a filtered set of descriptors using the plurality of physico-chemical and structural descriptors; generating a plurality of fingerprint categories based on the plurality of Molecular Fingerprints (MF), wherein a first fingerprint category comprises a first set of fingerprints that is selected based on an occurrence threshold, wherein a second fingerprint category comprises a second set of fingerprints that is selected by applying at least one of a Chi-squared test and a Fisher's exact test on the plurality of Molecular Fingerprints (MF), wherein a third fingerprint category comprises a third set of fingerprints that is selected by applying an information gain statistical test on the plurality of Molecular Fingerprints (MF); generating a fourth fingerprint category comprising a fourth set of fingerprints that is selected based on a combination of the plurality of Molecular Fingerprints (MF) and the plurality of molecular fragments and the occurrence threshold; and performing one or more transformation techniques on the plurality of 2D and 3D structural images to obtain an optimized set of structural images. The one or more hardware processors are further configured by the instructions to: automatically generate a plurality of models based on the filtered set of descriptors, the first set of fingerprints, the second set of fingerprints, the third set of fingerprints, the fourth set of fingerprints and the optimized set of structural images respectively; automatically select and recommend a best model from the plurality of models based on the biological data and the plurality of chemical information; and automatically predict biological response of the chemical compound based on at least one of the best model and one or more user selected models from the plurality of models.

In an embodiment, the first set of fingerprints, the second set of fingerprints, the third set of fingerprints, and the fourth set of fingerprints comprise one or more CDK fingerprints, one or more CDK Extended fingerprints, one or more Estate fingerprints, one or more CDK Graph only fingerprints, one or more MACCS fingerprints, one or more Pubchem fingerprints, one or more Substructure fingerprints, one or more Klekota-Roth fingerprints, 2D Atom Pair fingerprints, one or more molecular fragments or combinations thereof.

In an embodiment, the first set of fingerprints comprises at least one of a Type I fingerprint, a Type II fingerprint, a Type III fingerprint and a Type IV fingerprint.

In an embodiment, the second set of fingerprints comprises a Type A fingerprint and a Type B fingerprint.

In an embodiment, the third set of fingerprints comprises a Type C fingerprint.

In an embodiment, the fourth set of fingerprints comprises at least one of a Type I fingerprint, a Type II fingerprint, a Type III fingerprint and a Type IV fingerprint.

In an embodiment, the step of applying one or more statistical analysis techniques on the one or more physico-chemical and structural descriptors to obtain a filtered set of statistically significant descriptors comprises eliminating information or descriptors having zero or low variance and the like from data specific to the one or more physico-chemical and structural descriptors.

In an embodiment, a presence of Type I fingerprint in at least one of the first set of fingerprints and the fourth set of fingerprints indicates contribution of the Type I fingerprint to one of a biological response, an adverse event or an activity of the chemical compound, for example toxicity.

In an embodiment, an absence of a Type II fingerprint in at least one of the first set of fingerprints and the fourth set of fingerprints indicates contribution of the Type II fingerprint to a biological response, an adverse event or an activity of the chemical compound, for example toxicity.

In an embodiment, a presence of a Type III fingerprint in at least one of the first set of fingerprints and the fourth set of fingerprints indicates contribution of the Type III fingerprint in no activity, no adverse event or non-toxicity of the chemical compound.

In an embodiment, an absence of a Type IV fingerprint in at least one of the first set of fingerprints and the fourth set of fingerprints indicates contribution of the Type IV fingerprint in no activity, no adverse event or non-toxicity of the chemical compound.

In an embodiment, a first model (or Model I) from the plurality of models is generated based on the filtered set of descriptors, the first set of fingerprints, classification models such as support vector machine and random forest or combinations thereof.

In another embodiment, a second model (Model II) from the plurality of models is generated based on the first set of fingerprints, and occurrence of each type of first set of fingerprints in a chemical compound.

In an embodiment, the third model (Model III) is generated based on a probability of at one of the activity, biological response or adverse event levels (for example, toxic and non-toxic) in the second set of fingerprints and the third set of fingerprints.

In an embodiment, the fourth model (Model IV) is generated based on the fourth set of fingerprints and occurrence of each type of fourth set of fingerprints in a chemical compound.

In an embodiment, the fifth model (Model V) is generated based on generated 2D and 3D structural images of chemical compounds and classification techniques such as deep neural networks.

In yet another aspect, there are provided one or more non-transitory machine readable information storage mediums comprising one or more instructions which when executed by one or more hardware processors causes automated prediction of biological response of a chemical compound using chemical information associated thereof by receiving biological data pertaining to chemical structure of a chemical compound; generating a plurality of chemical information for the chemical compound using associated molecular structure, wherein the plurality of chemical information comprise a plurality of physico-chemical and structural descriptors, a plurality of Molecular Fingerprints (MF), a plurality of molecular fragments, and a plurality of two-dimensional (2D) and three-dimensional (3D) structural images; applying one or more statistical analysis techniques on the plurality of chemical information to obtain a filtered chemical information, wherein the step of applying one or more statistical analysis techniques on the plurality of chemical information to obtain a filtered chemical information comprises: obtaining a filtered set of descriptors using the plurality of physico-chemical and structural descriptors; generating a plurality of fingerprint categories based on the plurality of molecular fingerprints, wherein a first fingerprint category comprises a first set of fingerprints that is selected based on an occurrence threshold, wherein a second fingerprint category comprises a second set of fingerprints that is selected by applying at least one of a Chi-squared test and a Fisher's exact test on the plurality of molecular fingerprints, wherein a third fingerprint category comprises a third set of fingerprints that is selected by applying an information gain statistical test on the plurality of molecular fingerprints; generating a fourth fingerprint category comprising a fourth set of fingerprints that is selected based on a combination of the plurality of molecular fingerprints and the plurality of molecular fragments and the occurrence threshold; and performing one or more transformation techniques on the plurality of 2D and 3D structural images to obtain an optimized set of structural images;

The instructions may further cause automatically generating a plurality of models based on the filtered set of descriptors, the first set of fingerprints, the second set of fingerprints, the third set of fingerprints, the fourth set of fingerprints and the optimized set of structural images respectively; automatically selecting and recommending a best model from the plurality of models based on the biological data and the plurality of chemical information; and automatically predicting biological response of the chemical compound based on at least one of the best model and one or more user selected models from the plurality of models.

In an embodiment, the first set of fingerprints, the second set of fingerprints, the third set of fingerprints, and the fourth set of fingerprints comprise one or more CDK fingerprints, one or more CDK Extended fingerprints, one or more Estate fingerprints, one or more CDK Graph only fingerprints, one or more MACCS fingerprints, one or more Pubchem fingerprints, one or more Substructure fingerprints, one or more Klekota-Roth fingerprints, 2D Atom Pair fingerprints, one or more molecular fragments or combinations thereof.

In an embodiment, the first set of fingerprints comprises at least one of a Type I fingerprint, a Type II fingerprint, a Type III fingerprint and a Type IV fingerprint.

In an embodiment, the second set of fingerprints comprises a Type A fingerprint and a Type B fingerprint.

In an embodiment, the third set of fingerprints comprises a Type C fingerprint.

In an embodiment, the fourth set of fingerprints comprise at least one of a Type I fingerprint, a Type II fingerprint, a Type III fingerprint and a Type IV fingerprint.

In an embodiment, the step of applying one or more statistical analysis techniques on the plurality of physico-chemical and structural descriptors to obtain a filtered set of statistically significant descriptors comprises eliminating information or physico-chemical and structural descriptors having zero or low variance and the like from data specific to the plurality of physico-chemical and structural descriptors.

In an embodiment, a presence of Type I fingerprint in at least one of the first set of fingerprints and the fourth set of fingerprints indicates contribution of the Type I fingerprint to one of a biological response, an adverse event or an activity of the chemical compound, for example toxicity.

In an embodiment, an absence of a Type II fingerprint in at least one of the first set of fingerprints and the fourth set of fingerprints indicates contribution of the Type II fingerprint to one of a biological response, an adverse event or an activity of the chemical compound, for example toxicity.

In an embodiment, a presence of a Type III fingerprint in at least one of the first set of fingerprints and the fourth set of fingerprints indicates contribution of the Type III fingerprint in no activity, no adverse event or non-toxicity of the chemical compound.

In an embodiment, an absence of a Type IV fingerprint in at least one of the first set of fingerprints and the fourth set of fingerprints indicates contribution of the Type IV fingerprint in no activity, no adverse event or non-toxicity of the chemical compound.

In an embodiment, a first model (or Model I) from the plurality of models is generated based on the filtered set of descriptors, the first set of fingerprints, classification models such as support vector machine and random forest or combinations thereof.

In another embodiment, a second model (Model II) from the plurality of models is generated based on the first set of fingerprints, and occurrence of each type of first set of fingerprints in a chemical compound.

In an embodiment, the third model (Model III) is generated based on a probability of at least one of the activity, biological response or adverse event levels (for example toxic and non-toxic) in the second set of fingerprints and the third set of fingerprints.

In an embodiment, the fourth model (Model IV) is generated based on the fourth set of fingerprints and occurrence of each type of fourth set of fingerprints in a chemical compound.

In an embodiment, the fifth model (Model V) is generated based on generated 2D and 3D structural images of chemical compounds and classification techniques such as deep neural networks.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Figure 1:
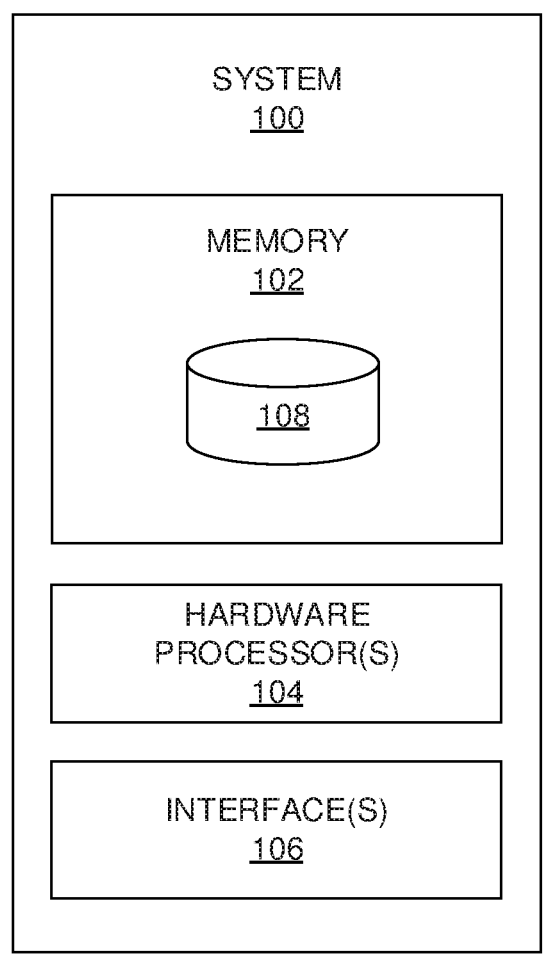
FIG. 1 illustrates an exemplary block diagram of a system 100 for automatically predicting biological response of a chemical compound using chemical information associated thereof in accordance with an embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Referring now to the drawings, and more particularly to FIGS. 1 through 6E, where similar reference characters denote corresponding features consistently throughout the figures, there are shown preferred embodiments and these embodiments are described in the context of the following exemplary system and/or method.

FIG. 1 illustrates an exemplary block diagram of a system 100 for automatically predicting biological response of a chemical compound using chemical information associated thereof in accordance with an embodiment of the present disclosure. The system 100 may also be referred as 'a prediction system' and interchangeably used hereinafter. In an embodiment, the system 100 includes one or more processors 104, communication interface device(s) or input/output (I/O) interface(s) 106, and one or more data storage devices or memory 102 operatively coupled to the one or more processors 104. The one or more processors 104 may be one or more software processing modules and/or hardware processors. In an embodiment, the hardware processors can be implemented as one or more microprocessors, microcomputers, microcontrollers, digital signal processors, central processing units, state machines, logic circuitries, and/or any devices that manipulate signals based on operational instructions. Among other capabilities, the processor(s) is configured to fetch and execute computer-readable instructions stored in the memory. In an embodiment, the device 100 can be implemented in a variety of computing systems, such as laptop computers, notebooks, hand-held devices, workstations, mainframe computers, servers, a network cloud and the like.

The I/O interface device(s) 106 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the I/O interface device(s) can include one or more ports for connecting a number of devices to one another or to another server.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment a database 108 can be stored in the memory 102, wherein the database 108 may comprise, but are not limited to information pertaining to chemical compound, chemical information, biological responses, rules or alerts, various models that are generated and executed for prediction of biological response, various fingerprints, images, occurrence threshold values, configuration details of the system during training phase and test/validation phase to perform the methodology described herein.

Figure 2:
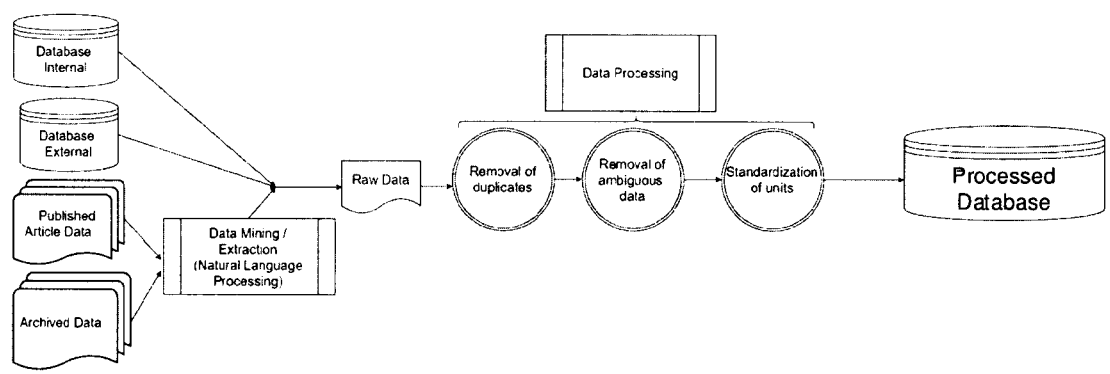
FIG. 2 illustrates an exemplary block diagram depicting a flow of processing raw data to extract biological data for predicting biological response of a chemical compound in accordance with an embodiment of the present disclosure.
Figure 3A:
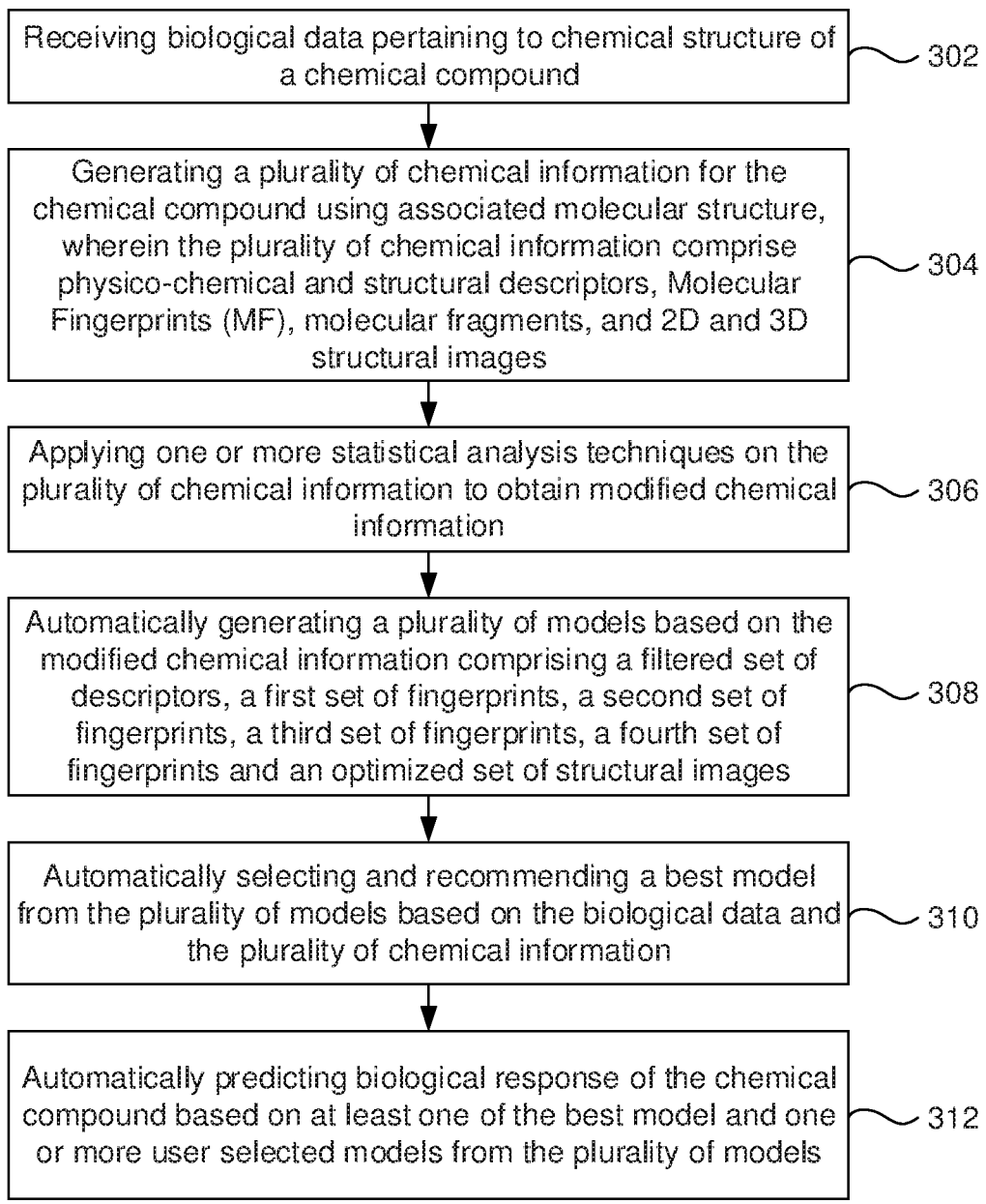
FIG. 3A illustrates an exemplary flow diagram of a method for automatically predicting biological response of a chemical compound based on the chemical information associated thereof using the system of FIG. 1 in accordance with an embodiment of the present disclosure.

FIG. 3A, with reference to FIG. 1, illustrates an exemplary flow diagram of a method for automatically predicting biological response of a chemical compound based on the chemical information associated thereof using the system 100 of FIG. 1 in accordance with an embodiment of the present disclosure. In an embodiment, the system(s) 100 comprises one or more data storage devices or the memory 102 operatively coupled to the one or more hardware processors 104 and is configured to store instructions for execution of steps of the method by the one or more processors 104. The steps of the method of the present disclosure will now be explained with reference to the components of the system 100 as depicted in FIGS. 1-2, FIG. 4, FIG. 5, FIGS. 6A through 6E, and the flow diagram of FIG. 3A-3B. In an embodiment of the present disclosure, at step 302, the one or more hardware processors 104 receive biological data pertaining to chemical structure of a chemical compound. In an embodiment, the biological data is extracted or derived from various sources (and/or databases, henceforth referred to as "raw data") and a critical evaluation of the data in different aspects such as duplicates, inconsistency in reported biological response (e.g., measurement units, compound IDs, Chemical structures, etc.) is performed. These inconsistencies affect the performances of computational models and there is a need for domain driven pre-processing approaches. FIG. 2, with reference to FIG. 1, illustrates an exemplary block diagram depicting a flow of processing raw data to extract biological data for predicting biological response of a chemical compound in accordance with an embodiment of the present disclosure. As can be seen from FIG. 2, raw data can be sourced from various databases, for example, internal database (or also referred as proprietary database), external database(s) (or also referred as 'external service providers, for example, PubChem that is a database of chemical molecules and their activities against biological assays, open source providers), published article(s) (e.g., patent applications, journals, literature, and the like), archived data, and the like. Raw (biological or chemical) data, for example, may comprise biological, chemical and physical information of compounds such as toxicity profile, partition coefficient, dipole moment, binding affinity, in vitro receptor data etc. in one or more file formats. To extract relevant information from such raw data, the system 100 performs automated pre-processing for example, natural language processing technique(s) and/or data mining techniques may be applied to derive the final input biological data for modelling studies. An example of an automated data pre-processing is presented in FIG. 2 in which the system 100 process the raw data through data processing technique(s) which includes a) identifying duplicate data entries and removal thereof, removal of ambiguous data (for example, with more than one different labels across various data sources), b) standardization of units (as units of raw data may be vary since they are obtained from various sources), and the like. For example, raw data obtained from source 1 may have unit specified in milligrams, while it may so happen that same raw data obtained from source 2 may have unit specified in micrograms and others. Therefore, taking into account all these constraints, the system 100 processes the raw data to obtain the final input biological data that is required in a specific format which gets stored in the processed database (e.g., also referred as database 108 of FIG. 1).

Thus in-short, input data for the toxicity prediction can be from various sources such as: internal database(s), external database(s), information extracted from published articles and archived data repositories using natural language processing, or data mining techniques, etc.

Figure 3B:
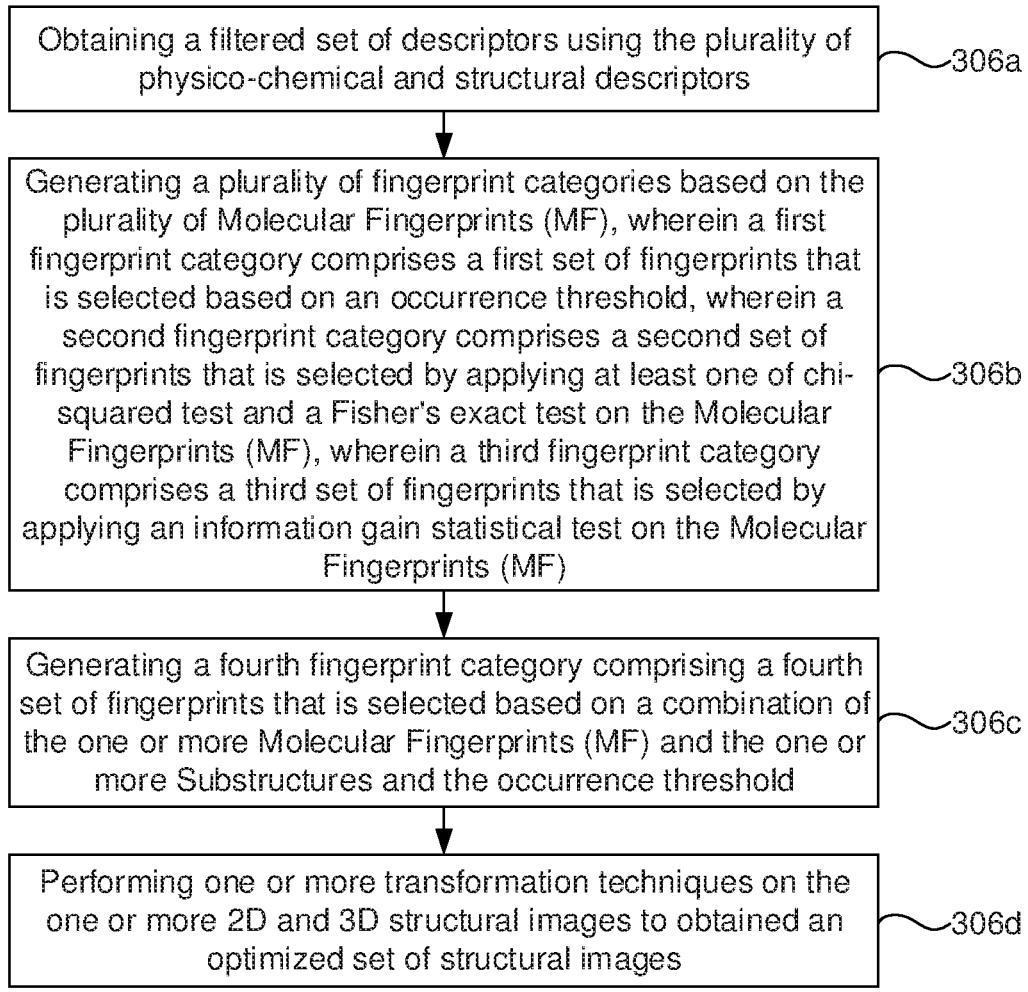
FIG. 3B illustrates an exemplary flow diagram of a method for applying one or more statistical analysis techniques on a plurality of chemical information to obtain filtered chemical information, in accordance with an embodiment of the present disclosure.
Figure 4:
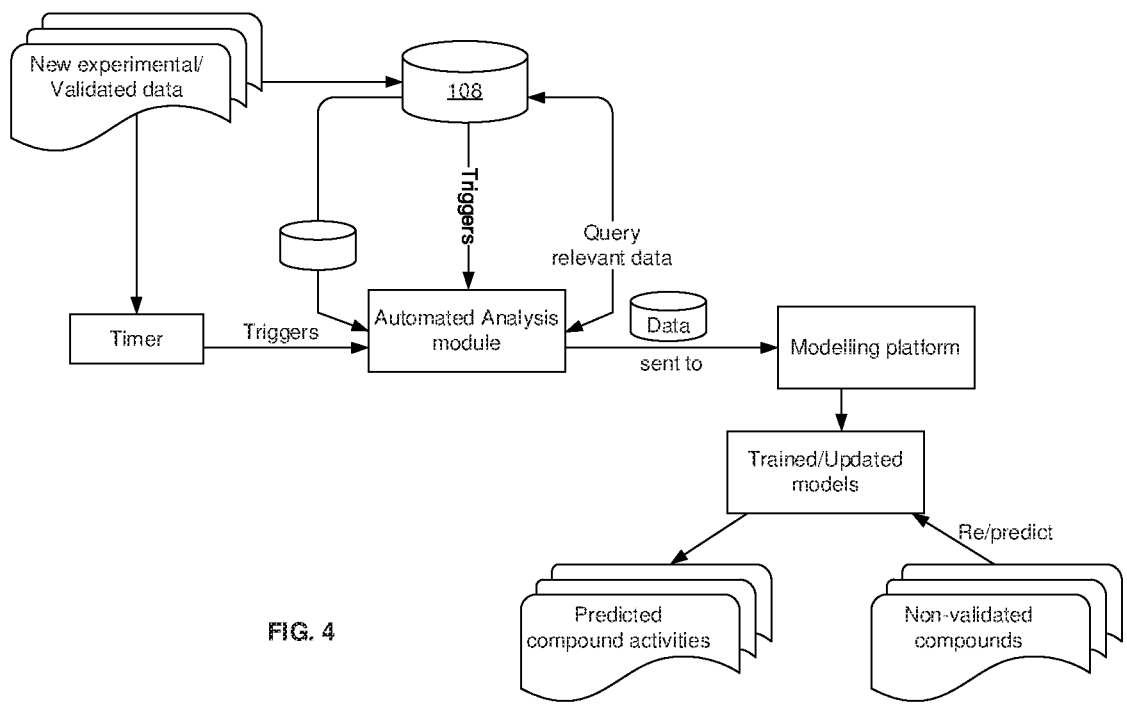
FIG. 4 illustrates an example scenario of the system 100 for predicting biological responses, in accordance with an embodiment of the present disclosure.
Figure 5:
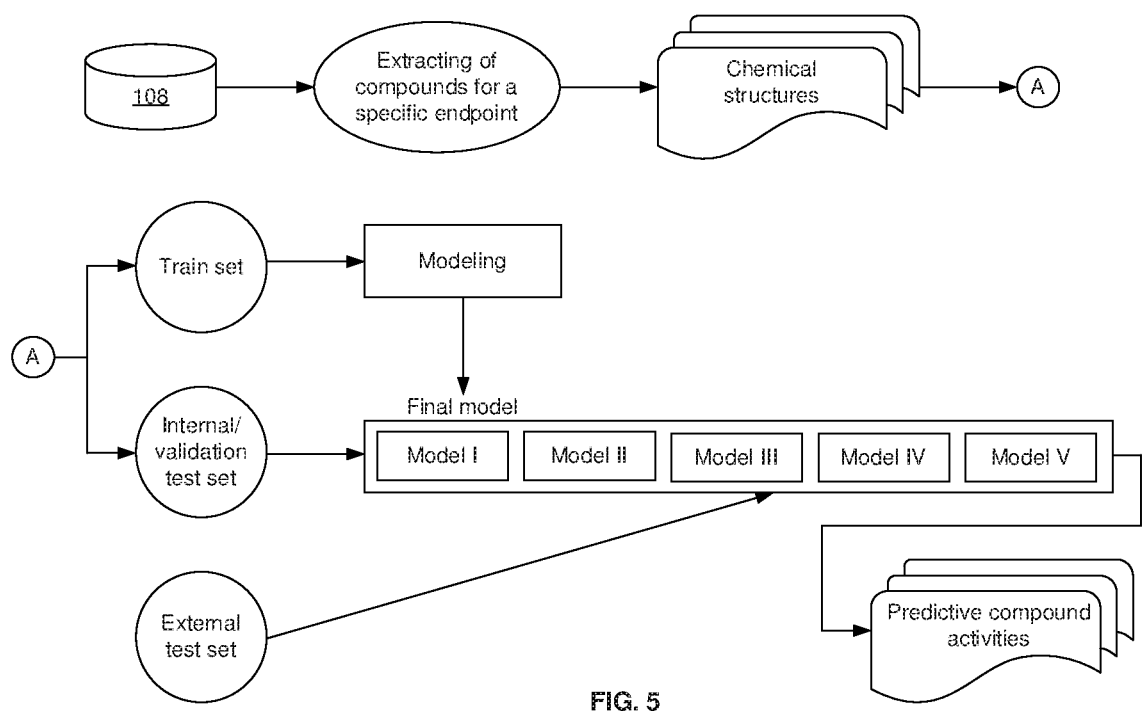
FIG. 5 is a high level block diagram for automatic prediction of biological response of a chemical compound according to some embodiments of the present disclosure.

The processed data, referred to as input data can be used for modeling purposes. Subsequently, to model a biological response/activity, examples, cardiotoxicity, renal toxicity etc., chemical information of the compounds are generated and used along with the biological response of the compounds. For example, if a specific end point is renal toxicity that needs to be modeled, relevant data such as chemical structure, assay conditions, biological response data etc. pertaining to this end point needs to be extracted from the processed database (e.g., also referred as database 108 of FIG. 1). This relevant information refers to chemical structure (or biological data) as described in step 302 that is used for generating models for predicting compound activities (or biological response) as depicted in FIG. 4, wherein various information from the chemical structure (or chemical information or biological data) are extracted. Some (portion) of the above chemical information/structures (whose activity or biological response of a given end point is already known) are taken for training a model (proposed model of the system 100), while other portion of the chemical information is used to validate results of the built/trained model and whenever external compounds with or without the biological response are received by the system 100 a prediction is performed, in such cases, the trained model is used for biological response prediction as depicted in FIG. 4. The training of proposed model is now discussed in steps 304-310 of FIGS. 3A-3B with reference to FIGS. 6A through 6E.

Referring back to FIGS. 3A-3B, in an embodiment of the present disclosure, at step 304, the one or more hardware processors 104 generate a plurality of chemical information for the chemical compound using associated molecular structure. In an embodiment, the plurality of chemical information comprise a plurality of physico-chemical and structural descriptors, a plurality of molecular fingerprints, a plurality of molecular fragments, and a plurality of two-dimensional (2D) and three-dimensional (3D) structural images. Each of the plurality of physico-chemical and structural descriptors comprises continuous and discrete features or variables that describe properties of compounds such as molecular weight, number of double bonds, solubility, and the like. [References: Todeschini, R; Consonni, V. Handbook of Molecular Descriptors; Wiley-VCH, 2000, and Karelson, M. Molecular Descriptors in QSAR/QSPR in Drug Design; Wiley Interscience: New York, 2000] Molecular fingerprints refer to binary features, which indicate presence or absence of a set of predetermined molecular sub-structures, structural features such as rings, charges, and the like [References: Daylight Chemical Information Systems, https://www.ics.uci.eduhdock/manuals/DaylightTheoryManual/index.html]. Molecular fragments are generated by cleaving the bonds based on various rules for example never break a bond that is part of a ring structure. These molecular fragments may be generated using open source tools such as SARpy (Thomas Ferrari, Giuseppina Gini, Nazanin Golbamaki Bakhtyari, Emilio Benfenati. "Mining Toxicity Structural Alerts from SMILES: A New Way to Derive Structure Activity Relationships" 2011 IEEE Symposium on Computational Intelligence and Data Mining (CIDM), Paris, 2011, pp. 120-127. doi: 10.1109/CIDM.2011.5949444) and Open Babel, (N M O'Boyle, M Banck, C A James, C Morley, T Vandermeersch, and G R Hutchison. "Open Babel: An open chemical toolbox." J. Cheminf. (2011), 3, 33. doi:10.1186/1758-2946-3-33 and The Open Babel Package, version 2.3.1 http://openbabel.ora), internal rules or combinations thereof. 2D and 3D structural images refer to images of geometrical orientation of a chemical compound as seen in 2D and/or 3D planes. In the present disclosure, color coding has been applied for different elements of the chemical image of a compound. For example, 'blue color coding for carbon atoms', and 'red color coding for oxygen atoms' etc. in the images. Further different color coding may be provided for single bond and double bond type. Color coding can be further provided for orientation of atoms (e.g., atoms visualized at the back side in a 2D plane can be represented by yellow color).

In an embodiment of the present disclosure, at step 306, the one or more hardware processors 104 apply one or more statistical analysis techniques on the plurality of chemical information to obtain filtered chemical information. More specifically, FIG. 3B illustrates an exemplary flow diagram of a method for applying one or more statistical analysis techniques on the plurality of chemical information to obtain filtered chemical information, in accordance with an embodiment of the present disclosure. In an embodiment, the step of applying one or more statistical analysis techniques on the plurality of chemical information to obtain filtered chemical information comprises: obtaining (306*a*) a filtered set of descriptors using the plurality of physico-chemical and structural descriptors; generating (306*b*) a plurality of fingerprint categories based on the plurality of Molecular Fingerprints (MF), wherein a first fingerprint category comprises a first set of fingerprints that is selected based on an occurrence threshold, wherein a second fingerprint category comprises a second set of fingerprints that is selected by applying at least one of a Chi-squared test and a Fisher's exact test on the plurality of molecular fingerprints, wherein a third fingerprint category comprises a third set of fingerprints that is selected by applying an information gain statistical test on the plurality of molecular fingerprints; generating (306*c*) a fourth fingerprint category comprising a fourth set of fingerprints that is selected based on a combination of the plurality of molecular fingerprints and the plurality of molecular fragments and the occurrence threshold; and performing (306*d*) one or more transformation techniques on the plurality of 2D and 3D structural images to obtain an optimized set of structural images. The one or more transformation techniques comprise but are not limited to, upscaling and/or downscaling to various sizes apart from orientation to various angles, in one example embodiment.

In an embodiment of the present disclosure, the first set of fingerprints, the second set of fingerprints, the third set of fingerprints, and the fourth set of fingerprints comprise one or more CDK fingerprints, one or more CDK Extended fingerprints, one or more Estate fingerprints, one or more CDK Graph only fingerprints, one or more MACCS fingerprints, one or more Pubchem fingerprints, one or more Substructure fingerprints, one or more Klekota-Roth fingerprints, 2D Atom Pair fingerprints, one or more molecular fragments or combinations thereof.

Figure 6A:
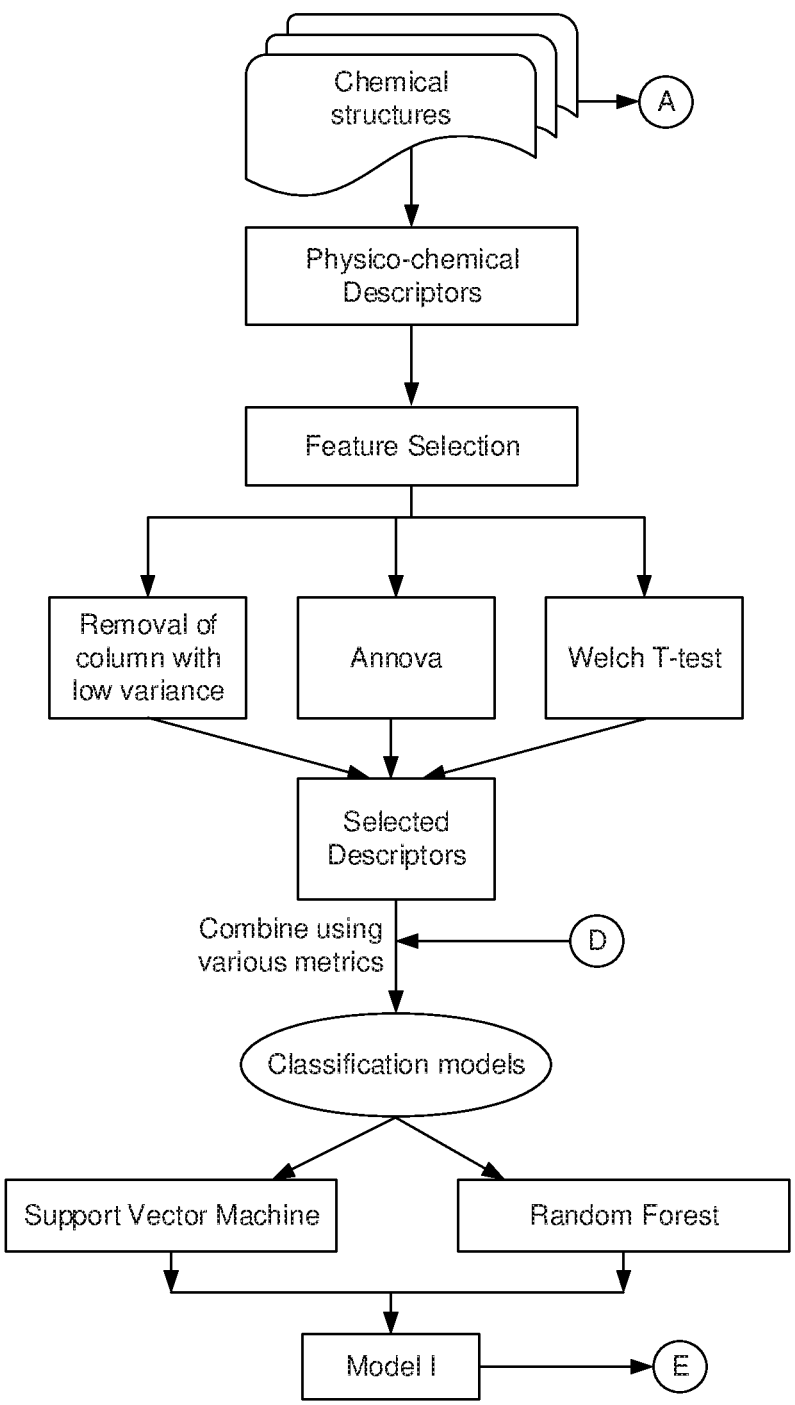
FIGS. 6A through 6E depicts a block diagram illustrating a method of automatically predicting biological response of a chemical compound using associated chemical information thereof in accordance with some embodiments of the present disclosure.

For better understanding of the above steps 306*a*-306*d*, the steps 306*a*-306*d* are described by way of examples below:

Statistical analysis technique(s) is/are applied on the chemical information (e.g., the physico-chemical and structural descriptors) for obtaining a filtered set of descriptors by removing zero or low variance columns and then the remaining are selected using various statistical measures (or feature selection technique(s)) such as one way analysis of variance (Annova), Welch t-test, and the like as depicted in FIG. 6A. This process is performed to select statistically significant variables that a) measure properties of a chemical compound, b) can be attributed to biological response of chemical compounds c) are not randomly related to the biological response and d) can, to an extent, be used to distinguish the compounds with respect to the activity/biological response. In an example case study, 352 physico-chemical and structural descriptors are generated by an in-house tool for 1049 chemical compounds by system 100. These 352 descriptors can be filtered using p-value from one way analysis of variance test to determine statistically significant variables. The system 100 may select descriptors having p-value less than 0.15 for further modelling, resulting in 83 filtered descriptors from 352 generated descriptors.

Figure 6B:
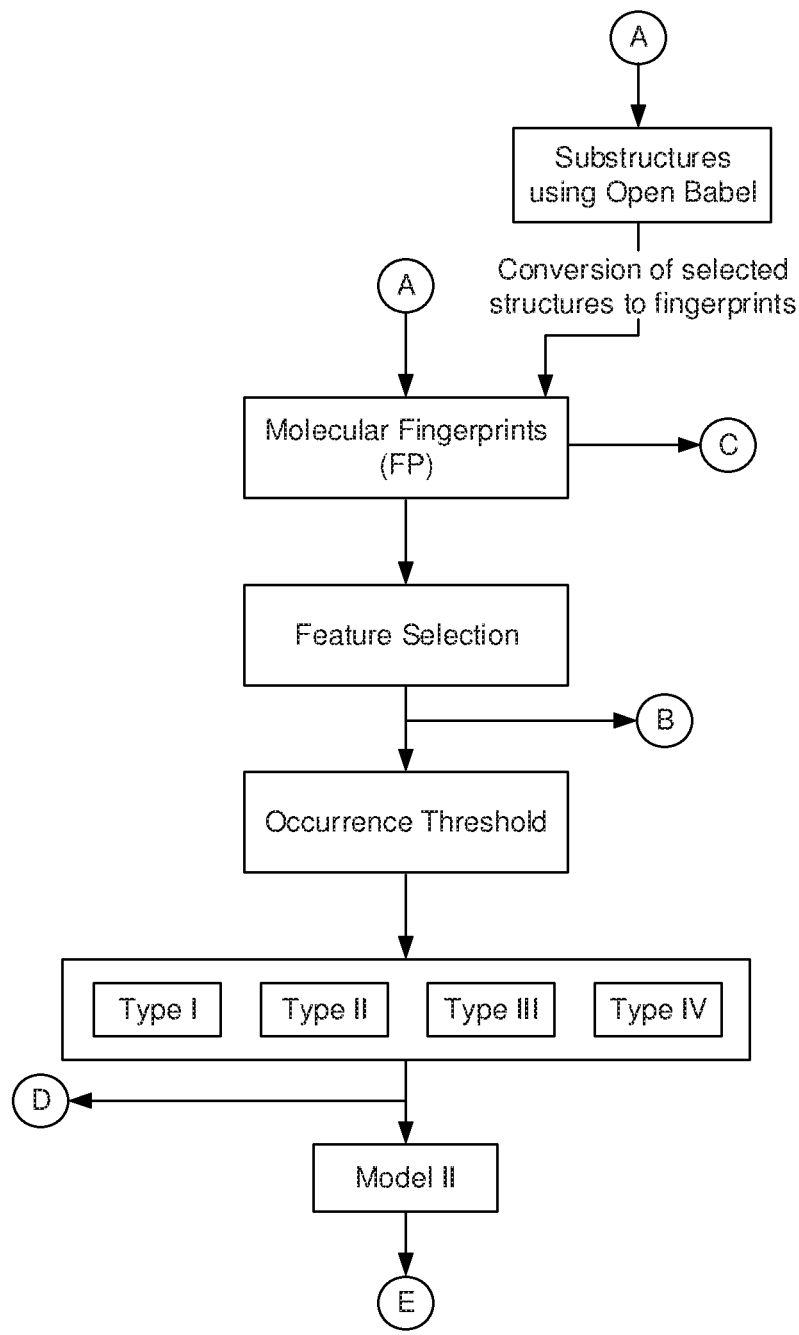

In the present disclosure, molecular fingerprints and molecular fragments are merged together as they describe similar information or attributes of chemical compounds. Subsequently, the generated molecular fingerprints and fragments are divided into broad categories based on the information they contain as follows:

A first fingerprint category comprises a first set of fingerprints that is (or are) selected based on an Occurrence Threshold (also referred as OT) as depicted in FIG. 6B, wherein minimum OT value can be 1. The first set of fingerprints comprises at least one of a Type I fingerprint, a Type II fingerprint, a Type III fingerprint and a Type IV fingerprint. For a fingerprint to be classified as a category 1 fingerprint, it has to occur in a minimum number of compounds called as Occurrence Threshold. For example, if a fingerprint (MF1) is observed only in 5 compounds and all these five compounds are toxic, then MF1 can be classified as Type I fingerprint if the occurrence threshold is less than 5. If the occurrence threshold is above 5 it cannot be classified as a category 1 fingerprint. Further, the occurrence threshold may vary (or varies) for each sub types of category 1 fingerprints depending on the composition of training dataset.

Figure 6C:
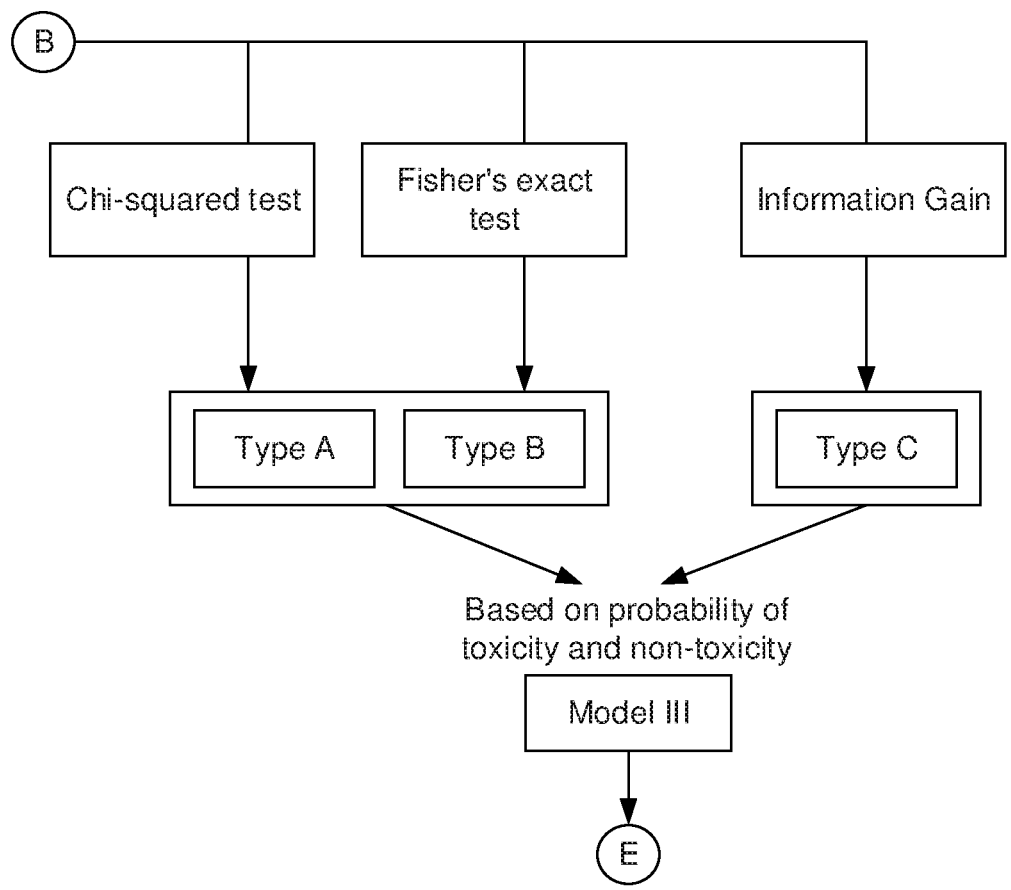
Figure 6D:
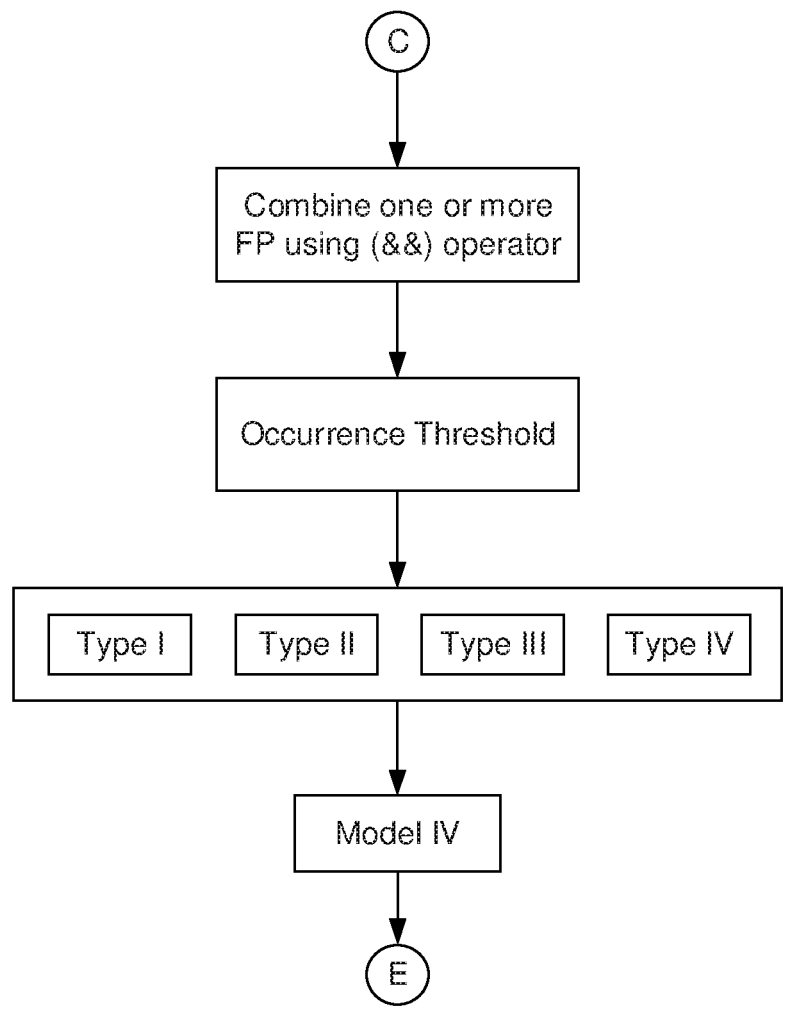

Presence of Type I fingerprint in at least one of the first set of fingerprints and the fourth set of fingerprints indicates contribution of the Type I fingerprint to one of a biological response, an adverse event or an activity of the chemical compound (for example toxicity). Similarly, absence of a Type II fingerprint in at least one of the first set of fingerprints and the fourth set of fingerprints indicates contribution of the Type II fingerprint to one of a biological response, an adverse event or an activity of the chemical compound (for example toxicity). Presence of a Type III fingerprint in at least one of the first set of fingerprints and the fourth set of fingerprints indicates contribution of the Type III fingerprint in no activity or (for example, non-toxicity) of the chemical compound. Likewise, absence of a Type IV fingerprint in at least one of the first set of fingerprints and the fourth set of fingerprints indicates contribution of the Type IV fingerprint no activity (for example, non-toxicity) of the chemical compound. The various fingerprint types are depicted in FIGS. 6B through 6D.

A second fingerprint category that comprises a second set of fingerprints that is (or are) selected by applying at least one of a Chi-squared test and a Fisher's exact test on the one or more Molecular Fingerprints (MF). The second set of fingerprints comprises a Type A fingerprint and a Type B fingerprint (based on Fisher's exact test) as depicted in FIG. 6C. In other words, Type A are fingerprints on which Chi-squared test can be applied and have a p-value below a user defined confidence level, in one example embodiment. Similarly, Type B are those on which Chi-squared test cannot be applied but are selected/filtered using Fisher's exact test and have a p-value below a user defined confidence level, in one example embodiment. A smaller p-value of a variable, in either of the two tests, indicates a stronger evidence against the hypothesis that the variable is not related to the biological response or activity of the chemical compounds. For example, the critical value of $\chi^2$ (Chi squared) with one degree of freedom at the 1 percent (p-value of 1% or 0.01) level is 6.635. If a fingerprint has a test statistic value below 6.635, system 100 may consider it to be statistically insignificant in differentiating the two classes (for example, toxicity and non-toxicity) in discussion. Thus, system 100 may select fingerprints whose test statistic is above 6.635 or p-value less than 0.01. In an example case study, 424 fingerprints were statistically significant in differentiating the two classes i.e., a p-value less than 0.01. The chi-squared test can be obtained from Karl Pearson, "On the criterion that a given system of deviations from the probable in the case of a correlated system of variables is such that it can be reasonably supposed to have arisen from random sampling" (PDF). Philosophical Magazine. Series 5. 50: 157-175. doi:10.1080/14786440009463897 and Fisher's exact test from Fisher, R. A. (1922). "On the interpretation of $\chi2$ from contingency tables, and the calculation of P". Journal of the Royal Statistical Society. 85 (1): 87-94. doi:10.2307/2340521 and Fisher, R. A. (1954). Statistical Methods for Research Workers. Oliver and Boyd. ISBN 0-05-002170-2.

A third fingerprint category comprises a third set of fingerprints that is (or are) selected by calculating an information gain value for one or more Molecular Fingerprints (MF). The third set of fingerprints comprises a Type C fingerprint as depicted in FIG. 5C. In other words, Type C are those fingerprints which are selected using information gain or entropy value. This process ranks the fingerprints based on the information content a fingerprint holds in distinguishing the various biological responses/activities or classes (for example toxicity and non-toxicity). The information gain (IG) values ranges from zero to one. A fingerprint with information gain value 1 can clearly distinguish the classes and a fingerprint with IG value 0 cannot distinguish among the classes. The cut off IG value to filter fingerprints can be user defined or dynamic based on the number of fingerprints the system 100 selects. For example, system 100 can choose 50 fingerprints with highest information values or choose fingerprints whose IG value is greater than 0.6.

In a nutshell, if the fingerprints does not fall in to any of the types of first fingerprint category they will be classified using to second or third fingerprint category tests. All the classified category or type of fingerprints are selected based on various statistical tests and convey statistically significant information about the end point that is to be modeled.

As discussed above generated substructures from all the chemical compounds of the training set are merged to generate a set of unique molecular fragments that are not already represented in the previously generated fingerprints. For example, one of the molecular substructures generated from the training set can be 4-Iodoaniline or Bromobenzene, whose structures are given below. These substructures are also represented in KlekotaRoth fingerprints and therefore, capture same properties of a chemical compound. Thus, these two generated molecular substructures can be removed as they are already captured by other fingerprints. These substructures then represent additional set of fingerprints and are classified similar to fingerprints into first, second and third fingerprint categories' sub classes.

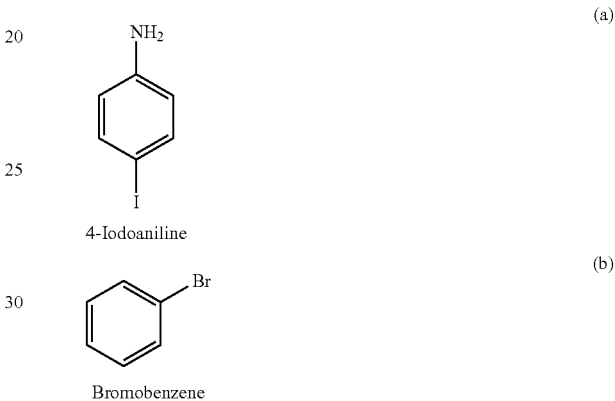

A fourth fingerprint category that comprises a fourth set of fingerprints that is (or are) selected based on a combination of the one or more molecular fingerprints and the molecular fragments and the occurrence threshold wherein the MFs and fragments are combined using '&&' (AND) operator. The fourth set of fingerprints comprise at least one of a Type I fingerprint, a Type II fingerprint, a Type III fingerprint and a Type IV fingerprint as depicted in FIG. 5D. In other words, in addition to the above fingerprints and fragments, the system 100 generates new combination of fingerprints by combining plurality of molecular fingerprints or fragments using 'AND' operator as depicted in FIG. 6D. For example, to generate a combined fingerprint (CFP1) using two fingerprints or of length two i.e., checking for presence of two fingerprints or fragments simultaneously, if a chemical compound contains both the fingerprints then the CFP1 value is represented as 1. If the chemical compound does not contain any of the two or both, then the value of CFP1 is taken as 0. In this manner, system 100 generates all possible combinations of two or more length fingerprints and then apply the same categorization (first fingerprint category: Type I, II, III and IV) as applied to original fingerprints. In the same example, let the FP1 be a KlekotaRoth fingerprint, whose substructure can be depicted as given in the figure below. Let FP2 be another PubChem fingerprint, whose substructure can be depicted as given in figure below. Now, CFP1 denotes a fingerprint that looks for the presence of both the substructures represented by FP1 and FP2 in any chemical compound. If both the substructures occur simultaneously in a chemical compound, the value of CFP1 is taken as 1 by the system 100. In all other scenarios the value of CFP1 is considered 0.

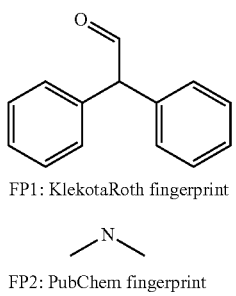

(a)

FP1: KlekotaRoth fingerprint (b)

FP2: PubChem fingerprint

In an embodiment, the occurrence threshold for the combined fingerprints may be user configurable and, in another, may vary from that of the original fingerprints. In yet another embodiment, the occurrence threshold may vary based on the training set available in the system 100. For instance, if training set contains toxic and non-toxic compounds in the ratio of 100:10 or 10:1, the occurrence threshold is set as 10 for Type I fingerprint, and for others the occurrence threshold is set as 1 as per the ratio. This ratio based on input data distribution is to ensure the model is not biased towards larger class of compounds. In other words, the ratio presents a solution to the problem of data imbalance as discussed in the introduction and observed in various biological response datasets. Additionally, the occurrence threshold may be dynamically changed as per the training set, learning pattern of the system 100 and the like. In an example embodiment, the system 100 may learn that the Type I occurrence threshold if set fifteen times larger than Type III occurrence threshold the model performance improves by 5%. The system 100 may set Type I occurrence threshold as 15 and Type III occurrence threshold as one. Similarly, system 100 can derive/learn rules for dynamic updation of occurrence thresholds of Type I, II, III and IV fingerprints. Consequently, system 100 also validates its rules across each new biological response prediction models it creates. Thus, system 100 learns these rules a) by observing performances across various biological response or adverse events prediction models, b) by varying the value of occurrence thresholds and c) from user inputs.

In an embodiment of the present disclosure, the first set of fingerprints, the second set of fingerprints, the third set of fingerprints, and the fourth set of fingerprints comprises one or more CDK fingerprints, one or more CDK Extended fingerprints, one or more Estate fingerprints, one or more CDK Graph only fingerprints, one or more MACCS fingerprints, one or more Pubchem fingerprints, one or more Substructure fingerprints, one or more Klekota-Roth fingerprints, 2D Atom Pair fingerprints, one or more molecular fragments or combinations thereof.

In an embodiment of the present disclosure, the system 100 generates structural images of chemical compounds in two and/or three dimensions. These images are color coded to represent an element, a type of bond, size of molecule, etc. with a particular color, uniformly across all compounds. As the size and orientation of similar bonds and cyclical structures varies across compounds depending on the number of atoms, system 100 can perform various transformations on the structural images, be it 2D or 3D, of the chemical compounds. For example, as shown below, in the structures of compounds x to y, the orientation and size of benzene ring varies across three different drug like molecules. The transformations on the structural images of chemical compounds can be rotation of the 2D in various degrees, up or down scaling original image to various sizes and the like, generating additional images and addressing some of the issues discussed above.

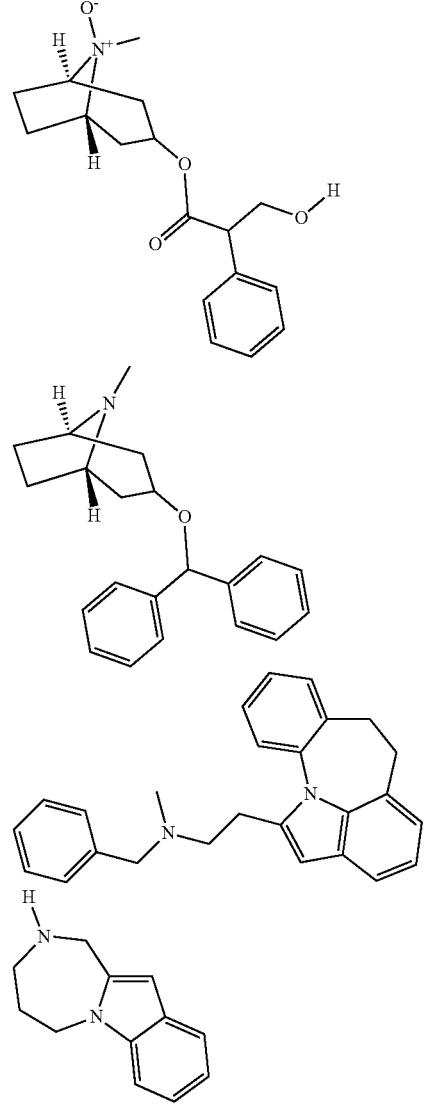

Referring back to FIG. 3A, in an embodiment of the present disclosure, at step 308, the one or more hardware processors 104 automatically generate a plurality of models based on the filtered set of descriptors, the first set of fingerprints, the second set of fingerprints, the third set of fingerprints, the fourth set of fingerprints and the optimized set of structural images respectively. In an embodiment, a first model (or Model I) from the plurality of models is generated based on the filtered set of descriptors, the first set of fingerprints, or combinations thereof. Model I may be generated using machine learning technique(s) for example, either support vector machine or a random forest. To train these models, a combination of one or more category 1, category 2 and filtered/selected descriptors are used to build a model. This model is validated and optimized on an internal test dataset and/or a validation set. The prediction of biological response may automatically done by the system 100 by utilizing model I which may be generated using the descriptors, Type I, Type II, Type III and Type IV fingerprints, or combinations thereof, in one example embodiment. In another example embodiment, it may so happen that biological response prediction may be automatically done by the system 100 using the model I that may be built without the use of descriptors, but only with Type I, Type II, Type III and Type IV fingerprints. In yet another embodiment the system 100 may predict half of the compounds only and the rest may be predicted by one or more of the model II, III, IV and V. One or more of these models may be preferred over another model based on the performance of individual models (model I, II, III, IV and V) built until then, on various datasets.

In an embodiment, a second model (model II) from the plurality of models is generated based on the first set of fingerprints (first fingerprint category) and occurrence of each type of first set of fingerprints in a chemical compound. In this, the system 100 uses the first set of fingerprints generated using the original fingerprints and fragments to predict the activity of the compounds. The activities or biological responses of chemical compounds for an end point are divided into various classes based on their value. For example toxicity as one class and non-toxicity as another class. Further, the system 100 computes class scores for each compound by verifying the presence or absence of each Type I, II, III, and IV fingerprints. Depending on these scores the system 100 assigns a class or predicts the biological response of a new compound.

In another embodiment, a third model (model III) from the plurality of models is generated based on the second set of fingerprints, third set of fingerprints, or combinations thereof. For each of the second and third set of fingerprints a set of probabilities values are computed. These probabilities represent various scenarios that can occur in a dataset. For example, in a two class classification model the set of probabilities, for each fingerprint can be pr(active/present), pr(inactive/absent), pr(inactive/present) and pr(inactive/absent). If a fingerprint (FP1) is present the probability of the compound to be active or toxic (probability of compound being active given that the fingerprint is present: pr(active/present) or probability(active/present)) is calculated from the training set values as below:

$$\text{probability(toxic} \mid FP1 \text{ is present)} = \frac{\text{number of training set compounds that contain } FP1 \text{ and are toxic}}{\text{number of training set compounds that contain } FP1}$$

Further, each of the second and third set of fingerprints are used for building model II only if the calculated probability scores, for each scenario as depicted above, lie outside the unpredictability range. This range indicates the level of confidence the system 100 needs in order to avoid incorrect classification, in view of the training set configuration.

In an example embodiment, and in a two class/level classification the unpredictable range can be calculated as follows. Let,
nBias: be the number of compounds in a class that has larger number of compounds in training set
nComp: be the total number of compounds in train set
threshold: be a user defined cut-off.

The system 100 calculates or defines distortion=(nBias/nComp)−0.5;

and then, the critical/unpredictable range is define as (LB-UB), where

Lower bound (LB): Minimum (threshold+distortion, threshold)

Upper bound (UB): Maximum (1−threshold+distortion,1−threshold)

Further, each of the second and third category fingerprint, which has its probability scores outside the unpredictability range, is used to calculate scores for each class or activity of a chemical compound. A class is then assigned to the compound based on the comparison of all the class scores. For example, let FP1 be a fingerprint, which can be represented structurally as in figure below and which has the following probability distribution.

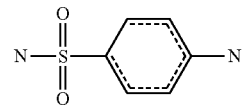

Probability set of Value
FP1
Pr (active|FP1=1) 0.92
Pr (active|FP1=0) 0.64
Pr (inactive|FP1=1) 0.08
Pr (inactive|FP1=0) 0.36

If the unpredictability range for the above example is (0.25-0.89), FP1 will be used for predicting activity of a compound given that the compound contains FP1 (i.e., FP1=1) in model III by system 100. If a compound does not contain FP1 (i.e., FP1=0), the probability set of FP1, and therefore FP1, will not be used in model III by system 100 as Pr (active|FP1=0) is within the unpredictable range. In another instance, if unpredictability range is (0.4, 0.6), FP1 will be used for modelling in both the presence and absence of FP1 fingerprint.

In an embodiment, subsequently, system 100 builds model III using all the second and third set of fingerprints filtered using unpredictability range. Using the probability set of each second and third set of fingerprints, the system 100 computes class scores for a chemical compound using a) presence or absence of the fingerprint FPX in the compound, b) probability score set of fingerprint FPX and c) summation and comparison of computed class scores.

In yet another embodiment, a fourth model (model IV) from the plurality of models is generated based on the fourth set of fingerprints, occurrence of each type of fourth set of fingerprints in a chemical compounds, or combinations thereof. In other words, combined fingerprints are used to assign class scores similar to model II.

In a further embodiment, a fifth model (model V) from the plurality of models is generated based on an analysis performed on the optimized set of structural images in a deep neural network. This model is generated using the images of chemical structures as input for a convolution deep neural network, in one example embodiment. The various models generated are depicted in FIGS. 6A through 6E.

Figure 6E:
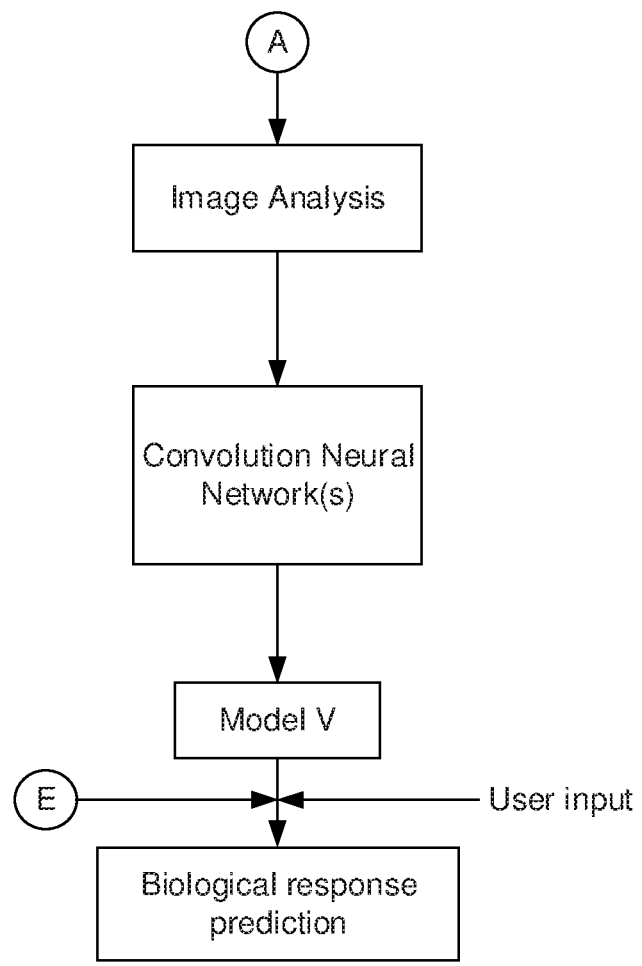

In an embodiment of the present disclosure, at step 310, the one or more hardware processors 104 automatically select and recommend a best model from the plurality of models based on the biological data and the plurality of chemical information, and at step 312, the one or more hardware processors 104 automatically predict biological response of the chemical compound based on at least one of the best model and one or more user selected models from the plurality of models. The term, "biological response" can be toxicity of chemicals, potency of drug candidates against a biological target in an in in vitro assay or in a cell based assay etc. It can be defined as the response exhibited by a biological system in in vitro, ex-vivo, in vivo conditions on exposure to a chemical, drug candidate etc. In an embodiment, the biological response of the chemical compound is predicted using the system recommended best model (and/or user selected models) as depicted in FIG. 6E wherein user provides his/her inputs by selecting at least one of the recommend best model(s) from the plurality of models or other models (not recommended by the system 100) from the plurality of models. The user selection may be based on information provided by the system 100 to the user. In one example embodiment, the information provided by system 100 may be a) specificity, sensitivity, area under ROC curve, and the like of all the built models, b) rules or insights developed from each built model and its supporting information or compounds that meet and do not meet the rules, etc. In one embodiment, automatically selection and recommendation of one or more models may be based on the a) output generated using feature selection technique(s) or b) optimization of predefined or user defined parameters for model(s) generation.

FIG. 4, with reference to FIGS. 1 through 3, illustrates an example scenario of the system 100 for predicting biological responses, in accordance with an embodiment of the present disclosure. In a nutshell, FIG. 4 illustrates automatic triggering of biological response modelling by an "Automated Analysis Module" for example, a) when new experimental data is available or b) after periodic time intervals. After each model is built/retrained, it is validated/verified against a set of compounds that are marked as "Validation Set" and the compounds with unknown biological responses are reclassified using the updated models.

Application of the above method(s) of the present disclosure (as depicted in FIGS. 2A through 6E) are better understood with the prediction of renal toxicity as the biological response as a representative example and the proposed system 100 to predict renal (kidney) toxicity. Kidney is one of the major target organs susceptible for drug induced renal toxicity as it is exposed to heavy metals, chemicals, fungal toxins, and a large number of drugs. Renal toxicity is often observed during clinical studies and further, the mechanisms of renal toxicity are not well understood as of date. Prediction of renal toxicity during preclinical drug development is a challenging problem owing to the poor predictivity of the animal models due to interspecies variability and it needs urgent attention. An alternate approach to address this problem would be to explore the chemical information residing within the drugs that induce renal toxicity and the published computational models/solutions as of date have met with limited success.

In the above example embodiment, the system 100 collected side effects data from SIDER 4.1 version and adverse drug reaction terms classification data from ADReCS website http://bioinf.xmu.edu.cn/ADReCS/index.jsp. Both these data (raw data) are used to construct biological response profiles (processed data) for various drug and drug like compounds (chemical compounds/structures) by performing various data processing techniques depicted in FIG. 2.

In the above example embodiment, for each chemical compound/structure, smiles are extracted using PubChem ID and are used to generate various chemical information as explained below:

Two types of variables were generated:
1. Fingerprints using Padel software version 2.21: these are binary variables taking values '1' or '0', indicating the presence or absence of a structural feature or substructure.
   a. CDK fingerprints: 1024 fingerprints for a various Atom Containers
   b. CDK Extended fingerprints: 1024 extended fingerprints for various Atom Containers that extends the CDK with additional bits describing ring features
   c. Estate fingerprints: 79 bit fingerprints using the E-State fragments. The E-State fragments are those described in [Hall, L. H. and Kier, L.B., Electro topological State Indices for Atom Types: A Novel Combination of Electronic, Topological, and Valence State Information, Journal of Chemical Information and Computer Science, 1995, 35:1039-1045].
   d. CDK Graph only fingerprints: 1024 specialized version of the CDK Fingerprints which does not take bond orders into account
   e. MACCS fingerprints: generates 166 bit MACCS keys whose SMARTS patterns were taken from RDKit
   f. Pubchem fingerprints: 881 fingerprints for a molecule
   g. Substructure fingerprints: Checks the presence of 307 SMARTS Patterns for Functional Group Classification by Christian Laggner
   h. Klekota-Roth fingerprints: 4860 SMARTS based substructure fingerprint based on Chemical substructures that enrich for biological activity [Klekota, Justin and Roth, Frederick P., Chemical substructures that enrich for biological activity, Bioinformatics, 2008, 24:2518-2525].
   i. 2D Atom Pair fingerprints: 780 fingerprints that check the presence of a set of atom pairs at various topological distances
2. Topological, geometrical, constitutional, and physicochemical descriptors using in house tool.

In addition to the above variables log P and log S values of the compounds were also included that are sourced from ALOGPS 2.1 (http://www.vcclab.org/lab/alogps/) in the analysis.

Further, the system 100 filters the generated chemical information using various criteria for example:
1. Statistically significant structural descriptors were selected using p-value calculated from one way analysis of variance test, which is applied continuous data used for predicting a categorical variable, toxicity. The system 100 may select only 83 descriptors for a p-value of less than 0.15, from generated 352 descriptors.
2. Category 1 fingerprints (Type I, Type II, Type III and Type IV) are selected by setting an occurrence threshold (OT) value. The minimum OT value can be 1. Using OT of 1, the system 100 filters 475 Type I fingerprints, 12 Type II fingerprints, 191 Type III fingerprints and no Type IV fingerprints.
3. After removing non-zero columns from all the remaining fingerprint data, the system categorizes the fingerprints with chi square value greater than a pre-defined threshold, for example 6.635, as Type A fingerprints and the remaining fingerprints as Type B fingerprints. In total, 424 Type A and 119 Type B were considered.

The above processing results in selection of 1221 out of 10,145 generated fingerprints and 83 out of 352 generated descriptors.

In an example embodiment, the system 100 can divide the processing data, consisting of 1114 (715 toxic and 399 non-toxic) compounds with 1221 fingerprint data and 1049 compounds with 83 descriptor data, into training and test data for model building and validation based on bitwise similarity. In an example scenario, the final datasets can be represented as follows:

Train Data: 847 compounds with 548 Toxic, and 299 Non-Toxic

Test Set: 267 compounds with 167 Toxic and 100 Non-Toxic

The system 100 in the above example maintained the ratio of toxic and non-toxic compounds in all the data sets approximately the same.

In the example case study considered above, dividing the processed data into training data and test data sets followed by fingerprint selection resulted in the below set of chemical information that can be used for model building
  a) Type I: 475 fingerprints
  b) Type II: 12 fingerprints
  c) Type III: 191 fingerprints
  d) Type IV: 0 fingerprints
  e) Type A: 424 fingerprints
  f) Type B: 119 fingerprints
  g) 83 Descriptors Each model built may be evaluated based on a number of metrics such as accuracy, sensitivity, specificity and percentage predicted. They are described in detail below:
  a) Accuracy: is the fraction of correct predictions. It can be mathematically defined as $$\text{Accuracy} = \frac{\text{Number of Correct Predictions}}{\text{Total Number of Predictions}}$$

b) Sensitivity: (also called the true positive rate, the recall, or probability of detection) measures the proportion of actual positives that are correctly identified as positives (e.g., the percentage of toxic compounds that are correctly identified or predicted as toxic). For a two way or binary classification model it can be defined as:

$$\text{Sensitivity} = \frac{\text{Number of Correctly identified Positives}}{\text{Total Number of Positives}}$$

c) Specificity: (also called the true negative rate) measures the proportion of actual negatives that are correctly identified as such (e.g., the percentage of non-toxic compounds that are predicted or identified as non-toxic compounds). For a two way or binary classification model it can be defined as:

$$\text{Specificity} = \frac{\text{Number of Correctly identified Negatives}}{\text{Total Number of Negatives}}$$

d) Percentage (%) Predicted: measures the proportion of compounds predicted by a model. It can be defined as:

$$\% \text{ Predicted} = \frac{\text{Number of Compounds predicted}}{\text{Total Number of Compounds}}$$

Final model was built based on 4 models: Model I, II, III and IV hierarchically, for example, if the compound is not predicted using model I, it was passed on to the next model(s), models II-V. Various combination of Model I, Model II, Model III, and Model IV (in the use case scenario) can also generate a final model. The final model combination for biological response prediction can be selected based on the highest percentage predicted, good sensitivity, specificity and accuracy in the test set.

Results for Model I using classifier as Random Forest are depicted below in illustrated table (Table 1). Predicted column in the table represents the total number of compounds predicted from a given set. Non-predicted columns represents the total number of compounds that are not classified in to any of the classes by the model. The relation between predicted and non-predicted can be defined as:

Set Size=Predicted Compounds+Non-Predicted Compounds

Similarly, the column accurate contains number of compounds that are correctly predicted by the model and inaccurate column contains the number of compounds that are wrongly or inaccurately classified by the model. Some of the other relations between the columns of the table are as follows:

Predicted Compounds =

Accurate Number of Compounds + Inaccurate Number of Compound $$\% \text{ Predicted} = \frac{\text{Predicted Compounds}}{\text{Set Size}}$$

A model with higher percentage of predicted compounds, with excellent sensitivity and specificity is preferred over models with lower percentage predicted, and relatively poor sensitivity or specificity.

TABLE 1

| Occurrence | Parameters | Set | Size | Predicted | Non-Predicted | Accurate | Inaccurate | Accuracy % | Percentage (%) Predicted | Sensitivity | Specificity |
|---|---|---|---|---|---|---|---|---|---|---|---|
| 1 | Tree count = 20, No. of attributes = 18 | Train | 847 | 801 | 46 | 800 | 1 | 99.87 | 94.56 | 1 | 1 |
|  |  | Test | 267 | 248 | 19 | 218 | 30 | 87.9 | 92.88 | 0.91 | 0.88 |

In this example embodiment, let a compound CX be Vidarabine (9-13-D-arabinofuranosyladenine) with its structure depicted in the figure below. This compound may contain substructures FPK1 and FPK2 KelkatoRoth Type I fingerprints. FPK1 and FPK2 can structurally be represented as given in figure below. The presence of these Type I fingerprints, FPK1 and FPK2, in the compound CX can indicate toxic characteristics of the compound. System 100, in similar way, checks for presence of all the first set of fingerprints to calculate toxic and non-toxic class scores for each compound. The class scores can be computed by counting the presence of each type of first set of fingerprints in a compound. In this example scenario, CX may be assigned toxic class score of 3 and non-toxic class score of 0, i.e., CX contains three Type I first set of fingerprints which indicate toxicity. Thus, CX can be classified as toxic by Model II.

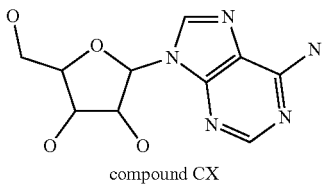
compound CX (a)

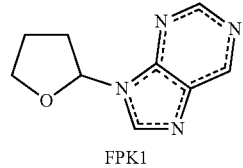
FPK1 (b)

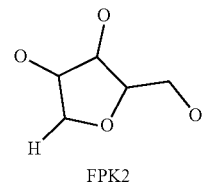
FPK2 (c)

Results for Model II for all compounds are depicted below in illustrated table (Table 2):

TABLE 2

| Occurrence Threshold | Set | Size | Predicted | Non-Predicted | Accurate | In-accurate | Accuracy % | Percentage (%) Predicted | Sensitivity | Specificity |
|---|---|---|---|---|---|---|---|---|---|---|
| 1 | Train | 847 | 484 | 363 | 484 | 0 | 100 | 57.14 | 1 | 1 |
|   | Test | 267 | 111 | 156 | 109 | 2 | 98.29 | 41.57 | 0.98 | 0.97 |

In this case study, System 100, computes following values for filtering fingerprints for building model III.
nBias=548
nComp=847
distortion=(548/857)−0.5=0.147
Using the above values, and a user defined or system defined threshold, system 100 computes the unpredictable range. For example for
threshold=0.15
Lower bound (LB)=Minimum (0.197, 0.15)=0.15
Upper bound (UB)=Maximum (0.997, 0.85)=0.99
Therefore, the unpredictability range is (0.15-0.99). In another scenario, if threshold=0.25, the unpredictable range can be computed as (0.25-0.89). Subsequently, system 100, filters second and third set of fingerprints using one of the unpredictable ranges and builds model III using probability class scores for each compound.

Results for Model III for two different unpredictable ranges are depicted below in illustrated table (Table 3):

TABLE 3

| Occurrence Threshold | Unpredictable | Set | Size | Predicted | Non-Predicted | Accurate | In-accurate | Accuracy % | Percentage (%) Predicted | Sensitivity | Specificity |
|---|---|---|---|---|---|---|---|---|---|---|---|
| 1 | 0.15, 0.99 | Train | 847 | 32 | 815 | 28 | 4 | 87.5 | 3.78 | 0 | 1 |
|   |   | Test | 267 | 6 | 261 | 5 | 1 | 83.33 | 2.25 | 0 | 1 |
| 1 | 0.25-0.89 | Train | 847 | 310 | 537 | 275 | 35 | 88.71 | 36.6 | 0.95 | 0.7 |
|   |   | Test | 267 | 73 | 194 | 69 | 4 | 94.5 | 27.35 | 1 | 0.84 |

In this example embodiment, let a compound CX be N-(1-Ethoxy-1-oxo-4-phenyl-2-butanyl) alanylproline with its structure depicted in the figure below. This compound may contain a combined fingerprint CFPX that checks for presence of fingerprints FPP, a PubChem fingerprint and FPK, a KelkatoRoth fingerprint. FPP and FPK can structurally be represented as given in figure below. System 100 checks for presence of all the fourth set of fingerprints, combined fingerprints, to calculate toxic and non-toxic class scores for each compound. The class scores can be probability of a compound to be toxic and nontoxic. It can also be computed by counting the presence of each type of fourth set of fingerprints. In this example scenario, CX may be assigned toxic class score of 19 and non-toxic class score of 0, i.e., CX satisfies 19 different Type I fourth set of fingerprints which indicate toxicity. Thus, CX can be classified as toxic by Model IV.

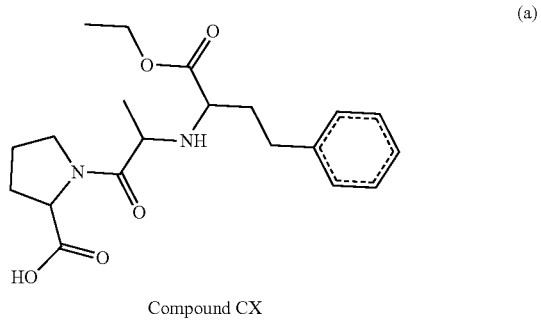

(a) Compound CX

(b) FPP fingerprint (c) FPK fingerprint

Results for Model IV for all compounds are depicted below in illustrated table (Table 4):

TABLE 4

| Type I Occurrence | Type III | Set | Size | Predicted | Non-Predicted | Accurate | In-accurate | Accuracy % | Percentage (%) Predicted | Sensitivity | Specificity |
|---|---|---|---|---|---|---|---|---|---|---|---|
| 10 | 10 | Train | 847 | 354 | 493 | 354 | 0 | 100 | 41.79 | 1 | 1 |
|  |  | Test | 267 | 116 | 151 | 105 | 11 | 90.5 | 43.44 | 1 | 0 |

Results for Combined models—Model II and III are depicted below in illustrated table (Table 5):

Model I: OT=1, Model II: Unpredictable Range (0.15, 0.99)

TABLE 5

| Set | Size | Predicted | Non-Predicted | Accurate | In-accurate | Accuracy % | Percentage (%) Predicted | Sensitivity | Specificity |
|---|---|---|---|---|---|---|---|---|---|
| Train | 847 | 498 | 349 | 497 | 1 | 99.79 | 58.79 | 0.99 | 1 |
| Test | 267 | 115 | 152 | 113 | 2 | 98.26 | 43.07 | 0.98 | 0.97 |

Results for combined models—Model II+Model III+Model IV are depicted below in illustrated table (Table 6):

Model 1 OT=1, Model II: Unpredictable Range (0.15, 0.99), Combination Thresholds: Type I=10, and Type III=10.

TABLE 6

| Set | Size | Predicted | Non-Predicted | Accurate | In-accurate | Accuracy % | Percentage (%) Predicted | Sensitivity | Specificity |
|---|---|---|---|---|---|---|---|---|---|
| Train | 847 | 584 | 263 | 583 | 1 | 99.83 | 68.94 | 0.99 | 1 |
| Test | 267 | 167 | 100 | 156 | 11 | 93.41 | 62.54 | 1 | 0.75 |

Best Results for combined models—Model I+Model II+Model III+Model IV are depicted below in illustrated table (Table 7):

Model 1 OT=1; Unpredictable range (0.15, 0.99); Combination Thresholds: Type I=10, and Type III=10; Random Forest: Tree=20, No. of Attributes=18

TABLE 7

| Set | Size | Predicted | Non-Predicted | Accurate | In-accurate | Accuracy % | Percentage (%) Predicted | Sensitivity | Specificity |
|---|---|---|---|---|---|---|---|---|---|
| Train | 847 | 847 | 0 | 846 | 1 | 99.88 | 100 | 0.99 | 1 |
| Test | 267 | 267 | 0 | 241 | 26 | 90.26 | 100 | 0.95 | 0.81 |

15

Best Result for Support Vector Machine (SVM) and Random Forest models, widely used classification techniques, with Fingerprints using Information Gain for feature selection are depicted below in illustrated table (Table 8):

TABLE 8

| Model | Set | Size | Accurate | Inaccurate | Accuracy % | Sensitivity | Specificity |
|---|---|---|---|---|---|---|---|
| SVM Kernel = RBF, C = 10, Gamma = 0.125 | Train | 847 | 836 | 11 | 98.7 | 0.99 | 0.96 |
|  | Test | 267 | 241 | 26 | 90.26 | 0.91 | 0.88 |
| Random Forest Tree count = 21, No. of Attributes = 4 | Train | 847 | 815 | 32 | 96.22 | 0.95 | 0.96 |
|  | Test | 267 | 240 | 27 | 89.88 | 0.88 | 0.92 |

Best Result for SVM and Random Forest models with Descriptors using ANOVA test for feature selection are depicted below in illustrated table (Table 9):

TABLE 9

| Model | Set | Size | Accurate | Inaccurate | Accuracy % | Sensitivity | Specificity |
|---|---|---|---|---|---|---|---|
| SVM Kernel = RBF, C = 2.0, Gamma = 0.125 | Train | 801 | 801 | 0 | 100 | 1 | 1 |
|  | Test | 248 | 153 | 95 | 61.69 | 1 | 0.01 |
| Random Forest Tree count = 21, No. of Attributes = 4 | Train | 801 | 798 | 3 | 99.62 | 0.998 | 0.993 |
|  | Test | 248 | 184 | 64 | 74.19 | 0.855 | 0.56 |

Best Result for SVM and Random Forest models with both Descriptors and Fingerprints are depicted below in illustrated table (Table 10). Feature selection done using ANOVA for Descriptors and Information Gain for Fingerprints:

TABLE 10

| Model | Set | Size | Accurate | Inaccurate | Accuracy % | Sensitivity | Specificity |
|---|---|---|---|---|---|---|---|
| SVM, Kernel = RBF C = 8, Gamma = 0.125 | Train | 801 | 801 | 0 | 100 | 1 | 1 |
|  | Test | 248 | 153 | 95 | 61.69 | 1 | 0.01 |
| Random Forest, Tree count = 25, No. of Attribute = 4 | Train | 801 | 800 | 1 | 99.87 | 1 | 0.99 |
|  | Test | 248 | 202 | 46 | 81.45 | 0.93 | 0.625 |

Prediction results using SARpy v1.0, Occurrence Threshold=1, Range of no. of atoms=(2, 18) are depicted below in illustrated table (Table 11).

TABLE 11

| Model | Set | Size | Predicted | Non-Predicted | Accurate | In-accurate | Accuracy % | Percentage (%) Predicted | Sensitivity | Specificity |
|---|---|---|---|---|---|---|---|---|---|---|
| Minimum Precision (Minimum likelihood ratio = 1) | Train | 847 | 846 | 1 | 666 | 180 | 78.72 | 99.88 | 0.87 | 0.62 |
|  | Test | 267 | 264 | 3 | 196 | 68 | 74.24 | 98.97 | 0.84 | 0.56 |
| Maximum Precision (Minimum Likelihood ratio = Infinity) | Train | 847 | 756 | 91 | 756 | 0 | 100 | 89.25 | 1 | 1 |
|  | Test | 267 | 165 | 102 | 144 | 21 | 87.27 | 61.79 | 0.95 | 0.66 |

The accuracy of 90.26 obtained by the current disclosure as depicted in Table 7 in comparison with the results of other modelling techniques presented in Tables 8-11 support the technical advantage of the current disclosure which can be observed in terms of prior defined statistical metrics. In addition, some of the insights that may be drawn by the system 100, the current disclosure, for the above example embodiment to predict renal toxicity, are a) the presence of one or more chemical sub-structures/structures depicted in Chemical structure below (e.g., Chemical structure 1) may result in toxic nature of a chemical compound b) the presence of one or more chemical structures depicted below (e.g., Chemical structure 2) may result in non-toxic nature of a chemical compound.

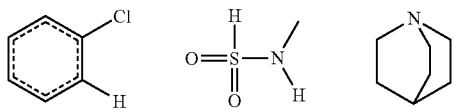

Chemical structure 1: Substructures that may result in renal toxicity of a chemical compound

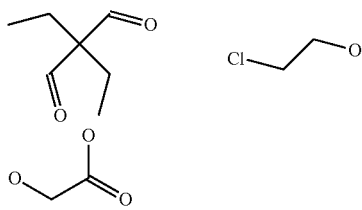

Chemical structure 2: Substructures that may not result in or may inhibit renal toxicity of a chemical compound The written description describes the subject matter herein to enable any person skilled in the art to make and use the embodiments. The scope of the subject matter embodiments is defined by the claims and may include other modifications that are relevant or occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed e.g., any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method, comprising:
receiving biological data pertaining to chemical structure of a chemical compound (302);
generating a plurality of chemical information for the chemical compound using associated molecular structure, wherein the plurality of chemical information comprise a plurality of physico-chemical and structural descriptors, a plurality of Molecular Fingerprints (MFs), a plurality of molecular fragments, and a plurality of 2D and 3D structural images (304);
applying one or more statistical analysis techniques on the plurality of chemical information to obtain filtered chemical information (306), wherein the step of applying one or more statistical analysis techniques on the plurality of chemical information to obtain filtered chemical information comprises:
 obtaining a filtered set of descriptors using the plurality of physico-chemical and structural descriptors (306 a);
 generating a plurality of fingerprint categories based on the plurality of molecular fingerprints, wherein a first fingerprint category comprises a first set of fingerprints that is selected based on an occurrence threshold, wherein a second fingerprint category comprises a second set of fingerprints that is selected by applying at least one of a chi-squared test and a Fisher's exact test on the plurality of molecular fingerprints, wherein a third fingerprint category comprises a third set of fingerprints that is selected by applying an information gain statistical test on the plurality of molecular fingerprints (306 b);
 generating a fourth fingerprint category comprising a fourth set of fingerprints that is selected based on a combination of the plurality of Molecular fingerprints and the plurality of molecular fragments and the occurrence threshold (306 c); and
 performing one or more transformation techniques on the plurality of 2D and 3D structural images to obtain an optimized set of structural images (306 d);
automatically generating a plurality of models based on the filtered set of descriptors, the first set of fingerprints, the second set of fingerprints, the third set of fingerprints, the fourth set of fingerprints and the optimized set of structural images respectively (308);
automatically selecting and recommending a best model from the plurality of models based on the biological data and the plurality of chemical information (310); and
automatically predicting biological response of the chemical compound based on at least one of the best model and one or more user selected models from the plurality of models (312).

2. The processor implemented method of claim 1, wherein the first set of fingerprints, the second set of fingerprints, the third set of fingerprints, and the fourth set of fingerprints comprise one or more CDK fingerprints, one or more CDK Extended fingerprints, one or more Estate fingerprints, one or more CDK Graph only fingerprints, one or more MACCS fingerprints, one or more Pubchem fingerprints, one or more Substructure fingerprints, one or more Klekota-Roth fingerprints, 2D Atom Pair fingerprints, one or more molecular fragments or combinations thereof.

3. The processor implemented method of claim 2, wherein a second model and a fourth model generated amongst the plurality of models are based on the first and fourth set of fingerprints respectively and the occurrence of each type of first and fourth set of fingerprints in a chemical compound.

4. The processor implemented method of claim 2, wherein a third model amongst the plurality of models is generated based on the probability of at least one of an activity, a biological response or an adverse event levels in the second set of fingerprints and the third set of fingerprints.

5. The processor implemented method of claim 1, wherein the first and fourth set of fingerprints comprises at least one of a Type I fingerprint, a Type II fingerprint, a Type III fingerprint and a Type IV fingerprint.

6. The processor implemented method of claim 5, wherein a presence of Type I fingerprint in at least one of the first set of fingerprints and the fourth set of fingerprints indicates contribution of the Type I fingerprint to one of a biological response, an adverse event or an activity of the chemical compound.

7. The processor implemented method of claim 5, wherein an absence of a Type II fingerprint in at least one of the first set of fingerprints and the fourth set of fingerprints indicates contribution of the Type II fingerprint to one of a biological response, an adverse event or an activity of the chemical compound.

8. The processor implemented method of claim 5, wherein a presence of a Type III fingerprint in at least one of the first set of fingerprints and the fourth set of fingerprints indicates contribution of the Type III fingerprint in one of no activity, no adverse event, or non-toxicity of the chemical compound.

9. The processor implemented method of claim 5, wherein an absence of a Type IV fingerprint in at least one of the first set of fingerprints and the fourth set of fingerprints indicates contribution of the Type IV fingerprint in one of no activity, no adverse event, or non-toxicity of the chemical compound.

10. The processor implemented method of claim 1, wherein the second set of fingerprints comprises a Type A fingerprint and a Type B fingerprint, and wherein the third set of fingerprints comprises a Type C fingerprint.

11. The processor implemented method of claim 1, wherein the step of applying one or more statistical analysis techniques on the plurality of physico-chemical and structural descriptors to obtain a filtered set of statistically significant descriptors from data specific to the plurality of physico-chemical and structural descriptors.

12. A system (100), comprising:
a memory (102) storing instructions;
one or more communication interfaces (106); and
one or more hardware processors (104) coupled to the memory (102) via the one or more communication interfaces (106), wherein the one or more hardware processors (104) are configured by the instructions to:
receive biological data pertaining to chemical structure of a chemical compound;
generate a plurality of chemical information for the chemical compound using associated molecular structure, wherein the plurality of chemical information comprise a plurality of physico-chemical and structural descriptors, a plurality of molecular fingerprints, a plurality of molecular fragments, and a plurality of 2D and 3D structural images;
apply one or more statistical analysis techniques on the plurality of chemical information to obtain filtered chemical information, wherein the step of applying one or more statistical analysis techniques on the plurality of chemical information to obtain filtered chemical information comprises:
obtaining a filtered set of descriptors using the plurality of physico-chemical and structural descriptors;
generating a plurality of fingerprint categories based on the plurality of Molecular fingerprints, wherein a first fingerprint category comprises a first set of fingerprints that is selected based on an occurrence threshold, wherein a second fingerprint category comprises a second set of fingerprints that is selected by applying at least one of a chi-squared test and a Fisher's exact test on the plurality of Molecular fingerprints, wherein a third fingerprint category comprises a third set of fingerprints that is selected by applying an information gain statistical test on the plurality of molecular fingerprints;
generating a fourth fingerprint category comprising a fourth set of fingerprints that is selected based on a combination of the plurality of molecular fingerprints and the plurality of molecular fragments and the occurrence threshold; and
performing one or more transformation techniques on the plurality of 2D and 3D structural images to obtain an optimized set of structural images;
automatically generate a plurality of models based on the filtered set of descriptors, the first set of fingerprints, the second set of fingerprints, the third set of fingerprints, the fourth set of fingerprints and the optimized set of structural images respectively;
automatically select and recommend a best model from the plurality of models based on the biological data and the plurality of chemical information; and
automatically predict biological response of the chemical compound based on at least one of the best model and one or more user selected models from the plurality of models.

13. The system of claim 12, wherein the first set of fingerprints, the second set of fingerprints, the third set of fingerprints, and the fourth set of fingerprints comprise one or more CDK fingerprints, one or more CDK Extended fingerprints, one or more Estate fingerprints, one or more CDK Graph only fingerprints, one or more MACCS fingerprints, one or more Pubchem fingerprints, one or more Substructure fingerprints, one or more Klekota-Roth fingerprints, 2D Atom Pair fingerprints, one or more molecular fragments or combinations thereof.

14. The system of claim 13, wherein a second model and a fourth model generated amongst the plurality of models are based on the first and fourth set of fingerprints respectively and the occurrence of each type of first and fourth set of fingerprints in a chemical compound, and wherein a third model amongst the plurality of models is generated based on the probability of at least one of an activity, a biological response or an adverse event levels in the second set of fingerprints and the third set of fingerprints.

15. The system of claim 12, wherein the first and fourth set of fingerprints comprises at least one of a Type I fingerprint, a Type II fingerprint, a Type III fingerprint and a Type IV fingerprint.

16. The system of claim 15, wherein a presence of Type I fingerprint in at least one of the first set of fingerprints and the fourth set of fingerprints indicates contribution of the Type I fingerprint to one of a biological response, an adverse event or an activity of the chemical compound.

17. The system of claim 15, wherein an absence of a Type II fingerprint in at least one of the first set of fingerprints and the fourth set of fingerprints indicates contribution of the Type II fingerprint to one of a biological response, an adverse event or an activity of the chemical compound.

18. The system of claim 15, wherein a presence of a Type III fingerprint in at least one of the first set of fingerprints and the fourth set of fingerprints indicates contribution of the Type III fingerprint in one of no activity, no adverse event, or non-toxicity of the chemical compound, and wherein an absence of a Type IV fingerprint in at least one of the first set of fingerprints and the fourth set of fingerprints indicates contribution of the Type IV fingerprint in no activity, no adverse event, or non-toxicity of the chemical compound.

19. The system of claim 12, wherein the second set of fingerprints comprises a Type A fingerprint and a Type B fingerprint, and wherein the third set of fingerprints comprises a Type C fingerprint.

20. The system of claim 12, wherein the step of applying one or more statistical analysis techniques on the plurality of physico-chemical and structural descriptors to obtain a filtered set of statistically significant descriptors from data specific to the plurality of physico-chemical and structural descriptors.

* * * * *